United States Patent
Kaczmarek et al.

(10) Patent No.: US 10,837,933 B2
(45) Date of Patent: Nov. 17, 2020

(54) SYSTEM AND METHOD FOR DETECTING FLUID TYPE

(71) Applicant: Haemonetics Corporation, Braintree, MA (US)

(72) Inventors: Sarah Kaczmarek, Boston, MA (US); Bruno Piazzarolo, Waltham, MA (US); Samuel Vaughan, Somerville, MA (US)

(73) Assignee: Haemonetics Corporation, Boston, MA (US)

( * ) Notice: Subject to any disclaimer, the term of this patent is extended or adjusted under 35 U.S.C. 154(b) by 409 days.

(21) Appl. No.: 15/327,178

(22) PCT Filed: Jul. 21, 2015

(86) PCT No.: PCT/US2015/041273
§ 371 (c)(1),
(2) Date: Jan. 18, 2017

(87) PCT Pub. No.: WO2016/018671
PCT Pub. Date: Feb. 4, 2016

(65) Prior Publication Data
US 2017/0167997 A1    Jun. 15, 2017

Related U.S. Application Data

(60) Provisional application No. 62/029,849, filed on Jul. 28, 2014.

(51) Int. Cl.
*G01N 27/10* (2006.01)
*A61M 1/34* (2006.01)
(Continued)

(52) U.S. Cl.
CPC .......... *G01N 27/10* (2013.01); *A61M 1/3496* (2013.01); *A61M 1/367* (2013.01); *A61M 1/0209* (2013.01);
(Continued)

(58) Field of Classification Search
CPC ..... G01N 27/10; A61M 1/3496; A61M 1/367; A61M 1/0209; A61M 2205/18;
(Continued)

(56) References Cited

U.S. PATENT DOCUMENTS 6,044,691 A * 4/2000 Kenley .............. A61M 1/3639
73/40.5 R
8,287,724 B2   10/2012 Slepicka et al.
(Continued)

FOREIGN PATENT DOCUMENTS

| JP | 2011-075529 | 4/2011 |
| WO | WO 2011/087631 | 7/2011 |
| WO | WO 2012/037106 | 3/2012 |

OTHER PUBLICATIONS

Shane Thomas, Authorized officer United States Patent and Trademark Office (ISA), International Search Report—Application No. PCT/US2015/041273, dated Oct. 23, 2015, 17 pages, together with the Written Opinion of the International Searching Authority.
(Continued)

*Primary Examiner* — Tung X Nguyen
*Assistant Examiner* — Feba Pothen
(74) *Attorney, Agent, or Firm* — Sunstein LLP

(57) ABSTRACT

A system for detecting a fluid type within a blood processing device includes a voltage source for electrical connection to a first electrode and to a second electrode, and a resistor in series between the voltage source and the first and/or second electrode. The voltage source may apply a voltage across the first and second electrodes. The system also includes a voltage detector that is electrically connected to the resistor and measures a voltage drop across the resistor. A circuit electrically connected to the voltage detector determines the type of fluid in contact with the first and second electrode based, at least in part, upon the measured voltage drop.

15 Claims, 22 Drawing Sheets

(51) Int. Cl.
  *G01R 27/22*     (2006.01)
  *A61M 1/02*      (2006.01)
  *A61M 1/36*      (2006.01)

(52) U.S. Cl.
  CPC . *A61M 2205/18* (2013.01); *A61M 2205/3317* (2013.01); *A61M 2205/502* (2013.01); *A61M 2205/581* (2013.01); *A61M 2205/583* (2013.01); *G01R 27/22* (2013.01)

(58) Field of Classification Search
  CPC .... A61M 2205/3317; A61M 2205/502; A61M 2205/581; A61M 2205/583; G01R 27/22
  See application file for complete search history.

(56) References Cited

U.S. PATENT DOCUMENTS

| | | | |
|---|---|---|---|
| 9,138,520 B2 | 9/2015 | White et al. | |
| 10,010,663 B2* | 7/2018 | Meyer | A61M 1/3644 |
| 2003/0194894 A1* | 10/2003 | Wariar | A61M 1/16 |
| | | | 439/191 |
| 2007/0104616 A1* | 5/2007 | Keenan | A61B 5/14557 |
| | | | 422/400 |
| 2011/0165595 A1* | 7/2011 | Catanzaro | B01L 7/52 |
| | | | 435/7.21 |

OTHER PUBLICATIONS

European Patent Office, Extended European Search Report, 9 pgs., dated Feb. 28, 2018 (application No. 15826592.6).

\* cited by examiner

SYSTEM AND METHOD FOR DETECTING FLUID TYPE

PRIORITY

This patent application claims priority from U.S. Provisional Patent Application Ser. No. 62/029,849, filed Jul. 28, 2014, entitled, "SYSTEM AND METHOD FOR DETECTING FLUID TYPE," and naming Sarah Londal, Bruno Piazzarolo, Samuel Vaughan and Yuri Zimenkov as inventors, the disclosure of which is incorporated herein, in its entirety, by reference.

TECHNICAL FIELD

The present invention relates to fluid detection systems and method, and more particularly, to systems and methods for detecting the type of fluid passing through a line.

BACKGROUND ART

Apheresis is a procedure in which an individual blood component can be separated and collected from whole blood withdrawn from a subject. Typically, whole blood is withdrawn through a needle inserted into the subject's arm and transferred into a cell separator, such as a centrifugal bowl. Once the whole blood is separated into its various components (e.g., plasma, red blood cells, and platelets), one or more of the components can be collected from the centrifugal bowl. The remaining components can be returned to the subject along with a compensation fluid to make up for the volume of the removed component.

During the apheresis procedure, a number of fluids may be connected to the system to aid in the procedure. For example, the technician may connect a container of anticoagulant to the system to prevent the blood and blood components being processed from coagulating. Additionally, saline may be connected to the system and used during the separation procedure. In some instances, the saline may be returned to the donor as the compensation fluid mentioned above (e.g., to make up for the volume of any removed blood and/or blood components). Although saline is safe to return to the donor, too much anticoagulant delivered directly to the donor can be harmful to the donor, and perhaps fatal. For example, if the technician operating the system accidentally connects the wrong fluid source (e.g., if the technician connects a container of anticoagulant instead of saline), there is a risk that too much anticoagulant (instead of saline) may be returned to the donor which, as mentioned above may be harmful and/or fatal.

SUMMARY OF THE EMBODIMENTS

In a first embodiment of the invention, there is provided a system for detecting a fluid type within a blood processing device. The system may include a voltage source configured for electrical connection to a first electrode and to a second electrode, and configured to apply a voltage across the first and second electrodes. The system may also include (1) a resistor in series between the voltage source and one of the first and second electrodes, and (2) a voltage detector electrically connected to the resistor and configured to measure a voltage drop across the resistor. A circuit may be electrically connected to the voltage detector, and may determine the type of fluid in contact with the first and second electrode based, at least in part, upon the measured voltage drop.

In some embodiments, the system may include a housing defining the structure of the system. The housing may be configured to receive a section of tubing containing the first and second electrodes, thereby electrically connecting the voltage source with the first and second electrodes. The system (e.g., within the housing) may have a first contact and a second contact electrically connected to the voltage source. The first contact may contact the first electrode, and the second contact may contact the second electrode when the section of tubing is installed within the housing.

The system may also have a display configured to display the applied voltage, the measured voltage drop, the type of solution, and/or an alarm condition. For example, the system (e.g., a microcontroller in communication with the circuit) may generate an alarm when the circuit determines the fluid passing through the section of tubing to be a first solution (e.g., anticoagulant or saline). The alarm may be an audible alarm and/or a visual alarm. The circuit (e.g., a microcontroller) may control a valve located on tubing leading from the source of the fluid based upon the determined type of fluid. For example, the circuit may open the valve if the system determines the fluid to be saline. Alternatively, the circuit may close the valve if the system determines the fluid to be anticoagulant. The system may also have a valve that isolates the fluid in contact with the first and second electrode.

In additional embodiments, the first and second electrodes may be on opposite sides of the fluid. Alternatively, the first and second electrodes may be on the same side of the fluid. The circuit may send an alarm to the blood processing system if the circuit determines the fluid passing through the section of tubing is anticoagulant.

In accordance with further embodiments, a system for detecting a fluid type within a blood processing system may include a voltage source configured (1) for electrical connection to a first electrode and to a second electrode, and (2) to apply a voltage across the first and second electrodes. The system may also include a voltage detector and a circuit. The voltage detector may be electrically connected to the first and second electrodes, and may measure a voltage drop across the first and second electrodes. The circuit may be electrically connected to the voltage detector, and may determine the type of fluid in contact with the first and second electrode based, at least in part, upon the measured voltage drop.

In accordance with additional embodiments, a disposable set for a blood processing system may include a first section of tubing for fluidly connecting a fluid source and a blood processing system. For example, the disposable set may include a first connector configured to connect to the fluid source, and a second connector configured to connect with the blood processing system. The set may also include an electrode unit having a housing and a first and second electrode within the housing. The first and second electrode may contact fluid passing through the disposable set.

The electrode unit may be located on the first section of tubing. Alternatively, the electrode set may be located on a second section of tubing that extends from the first section of tubing. In such embodiments, the set may include a ventilation plug that is located at the end of the second section of tubing and that allows air to exit the second section of tubing. To prevent fluid in contact with the first and second electrode from re-entering the first section of tubing, the set may also have a valve located on the second section of tubing (e.g., upstream of the electrode unit). The valve may prevent fluid in contact with the first and second electrode from re-entering the first section of tubing when closed.

In other embodiments, the disposable set may include a first collection bag for collecting a first blood component, and the second connector may connect to a port on a blood component separation device within the blood processing system. The set may also have a valve that is located on the first section of tubing and that, when closed, prevents the flow of fluid through the disposable set (e.g., if the first connector is connected to an incorrect fluid source). For example, the electrode unit may be configured to interact with a system for detecting a type of fluid passing through the disposable set. The valve located on the first section of tubing may selectively allow and prevent the flow of fluid through the disposable set. The operation of the valve may be controlled by the system based upon the type of fluid detected.

In still further embodiments, a method for detecting a type of fluid within a blood processing system includes inserting at least a portion of a disposable set into a fluid type detection system. The disposable set may have a first connector, a second connector, and an electrode unit having a first and second electrode. The method may also include connecting the first connector to a fluid source, and allowing fluid within the fluid source to flow through the disposable set. The first and second electrode may contact at least a portion of the fluid, and the method may apply a voltage across the first and second electrodes, and measure a voltage drop. Based, at least in part, on the measured voltage drop, the method may then determine the type of fluid passing through the disposable set. In some embodiments, measuring the voltage drop may include measuring the voltage drop across the first and second electrodes. Additionally or alternatively, measuring the voltage drop may include measuring the voltage drop across a resistor in series with the first and second electrodes.

The fluid type detection system may include a housing defining the structure of the system, and inserting the portion of the disposable set may include inserting the portion of the disposable set in the housing to electrically connect a voltage source with the first and second electrodes. If the solution is determined to be anticoagulant, the method may generate an alarm. The method may also include displaying, on a display of the detection system, the applied voltage, the measured voltage drop, the type of solution, and/or an alarm condition.

In further embodiments, the method may include controlling a valve located on tubing leading from the fluid source based upon the determined type of fluid. For example, the method may open the valve if the fluid is determined to be saline. Alternatively, the method may close the valve if the fluid is determined to be anticoagulant. The fluid type detection system may be integrated with or in communication with a blood processing system. In such embodiments, the method may include sending an alarm to the blood processing system if the fluid is determined to be anticoagulant. The alarm may be an audible alarm and/or a visual alarm. The method may also control a valve configured to isolate fluid in contact with the first and second electrode.

In additional embodiments, a system for detecting a fluid type in a blood processing system includes a UV light source located on a first side of a fluid flow path, and a UV light detector located on an opposing side of the fluid flow path. The UV light source may shine a UV light through a fluid passing through the fluid flow path. The UV light detector may measure an amount of UV light transmission through the fluid passing through the fluid flow path. The system may also include a microcontroller electrically connected with the UV light detector. The microcontroller may determine the type of the fluid passing through the fluid flow path based, at least in part, on the measured UV light transmission. The microcontroller may also calculate the optical density of the fluid passing through the fluid flow path, and determine the type of fluid based upon the optical density. The UV light source may have a wavelength between 200 and 240 nm.

The system may also include a housing defining the structure of the system. The housing may receive a section of tubing defining the fluid flow path. The UV light source may be located on one side of the section of tubing, and the UV light detector may be located on the opposing side of the section of tubing. The system (or housing) may include a display configured to display the measured transmission, the optical density, and/or the type of fluid. The fluid detection system may generate an alarm (e.g., an audible and/or visible alarm) when the microcontroller determines the fluid passing through the section of tubing to be anticoagulant.

The system (e.g., the microcontroller) may control, based upon the determined type of fluid, a valve located on tubing leading from the source of the fluid. For example the microcontroller may open the valve if the fluid is saline, and/or close the valve if the fluid is anticoagulant. The system may be integrated with or in communication with a blood processing system. Additionally, the microcontroller may send an alarm to the blood processing system if the microcontroller determines the fluid passing through the section of tubing to be anticoagulant.

In accordance with additional embodiments, an electrode unit for a fluid detection system may include a housing, a first electrode, and a second electrode. The housing may define the structure of the electrode unit, and may have a first port, a second port, and a flow path extending between the first and second port. The first electrode may extend through a wall of the housing, and a portion of the first electrode may be exposed to the flow path. The second electrode may also extend through the wall of the housing, and a portion of the second electrode may be exposed to the flow path. The second electrode may be spaced from the first electrode, and the first and second electrode may be configured to contact fluid passing through the flow path.

In some embodiments, the first and second electrodes may be located on opposite sides of the flow path. Additionally or alternatively, the housing may include a first and second opening extending through the wall of the housing. The first electrode may be press-fit into the first opening and the second electrode may be press-fit into the second opening. The electrode unit may also have a first septum located within the first opening, and a second septum located within the second opening. The first electrode may be located within the first septum, and the first septum may create a seal around the first electrode. The second electrode may be located within the second septum, and the second septum may create a seal around the second electrode.

In additional embodiments, the electrode unit may include a first and second grasping member extending from the housing. The first grasping member may extend over the first electrode and protect the first electrode. The second grasping member may extend over the second electrode and protect the second electrode. The electrode unit may be configured to interact with a system for detecting a fluid type. The system may determine a type of fluid passing through the electrode unit.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Various embodiments of the present invention provide a system and method for determining the type of fluid connected to a blood processing system to ensure that the correct fluid is connected. Some embodiments measure a voltage drop across the fluid (or a resistor in series with the fluid) which, in turn, is used by the system to determine if the solution passing through a section of tubing is saline or anticoagulant (e.g., a citrate based anticoagulant). If the system/method determines that the wrong solution is connected, the system/method may generate an alarm and/or otherwise stop the flow of fluid. Details of illustrative embodiments are discussed below.

Figure 1A:
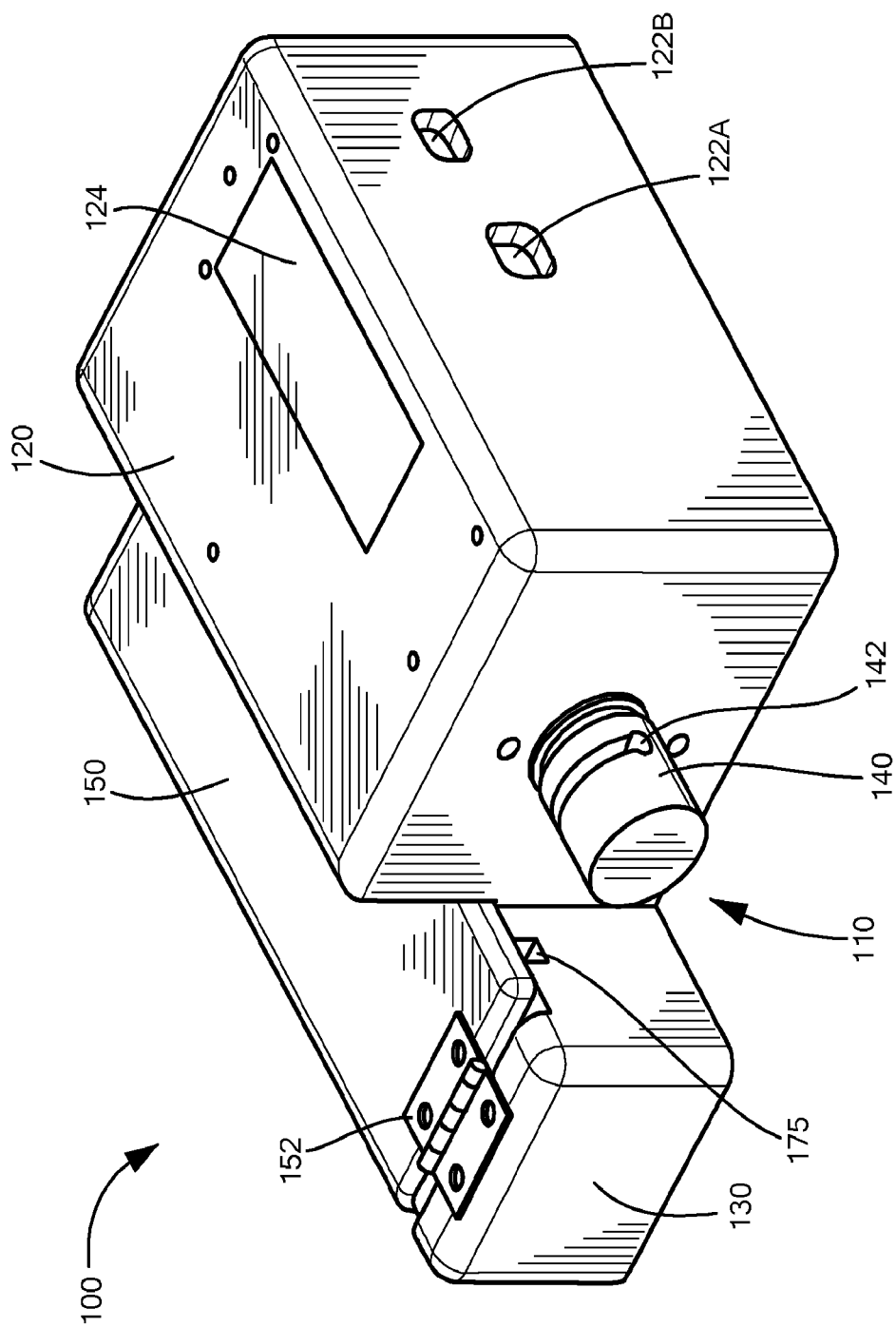
FIG. 1A schematically shows a perspective view of fluid type detection system in accordance with some embodiments of the present invention.
Figure 1B:
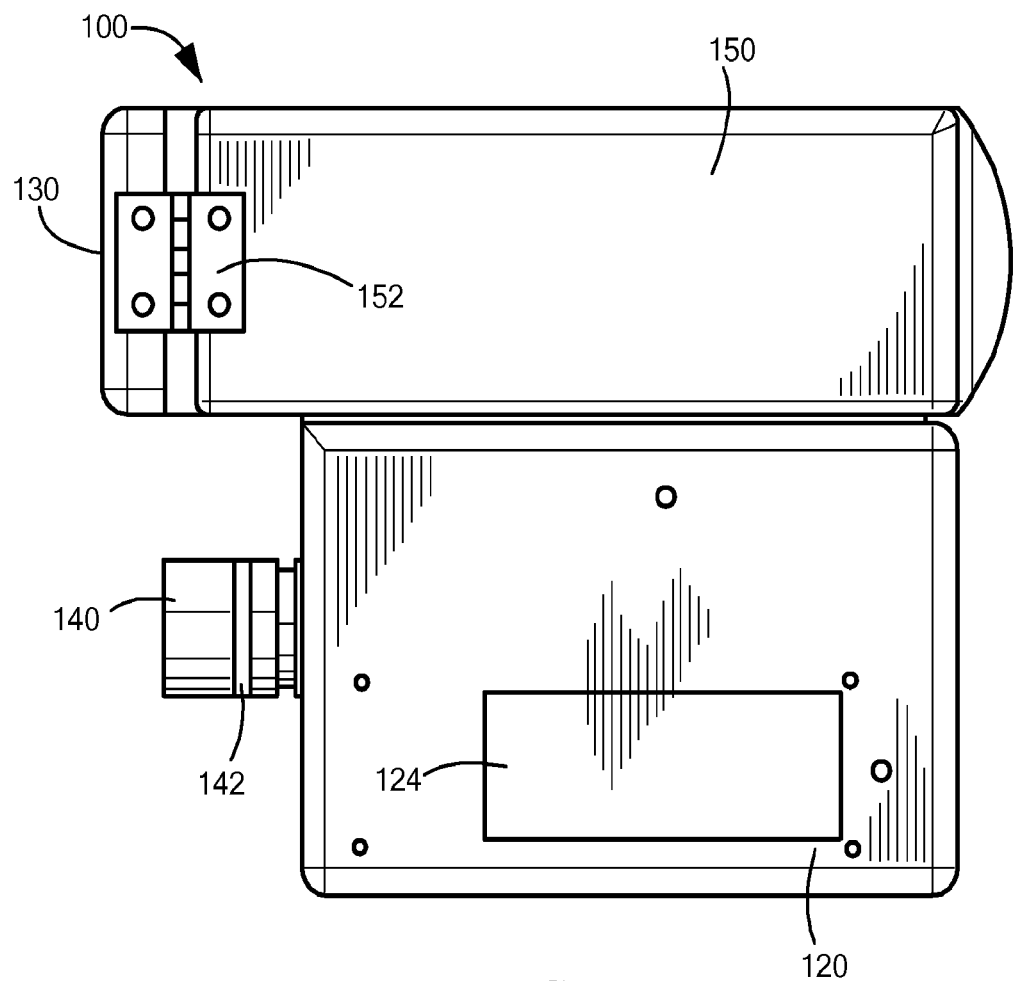
FIG. 1B shows a top view of the fluid type detection system of FIG. 1A, in accordance with some embodiments of the present invention.
Figure 1C:
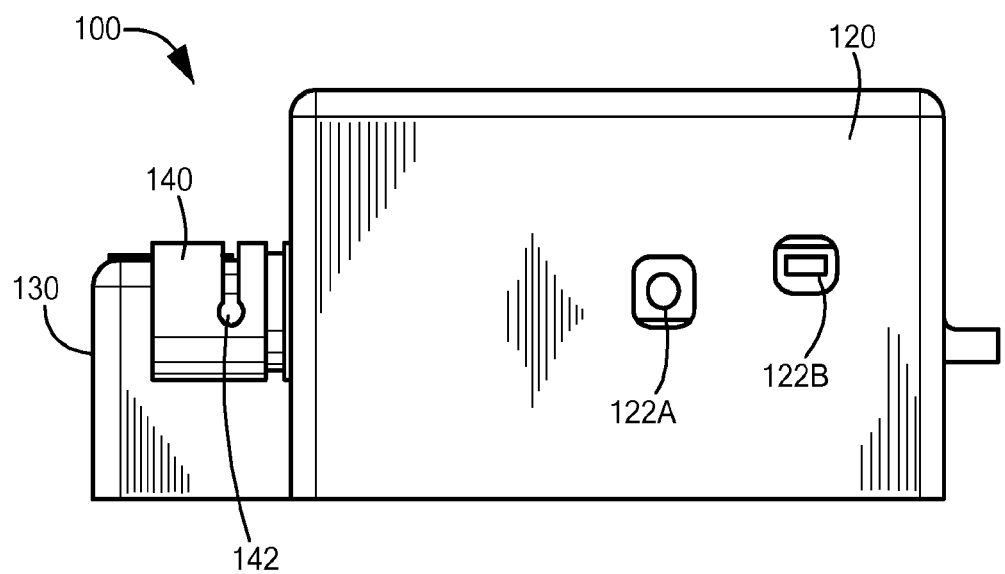
FIG. 1C shows a side view of the fluid type detection system of FIG. 1A, in accordance with some embodiments of the present invention.

FIGS. 1A to 1C show a system 100 for determining the type of fluid passing through a blood processing system. The system 100 may include a housing 110 that defines the structure of the system 100 and houses the required components. For example, the housing 110 may include a first portion 120 that houses the various electronic components required to determine the type of fluid (discussed in greater detail below). The first portion 120 of the housing 110 may include openings and/or electrical connections 122A/122B for connecting a power cable (not shown) and/or any required communication cables (e.g., so that the system 100 can communicate with the blood processing system). Additionally, the first portion 120 may include a display 124 (e.g., an LCD display). As discussed in greater detail below, during operation, the display 124 may show alarm messages, the type of fluid passing through a given section of tubing, and/or a measured resistance or voltage drop across the fluid (or the resistor).

Extending from one side of the first portion 120, the system 100 includes a valve 140 (e.g., a pinch valve) that selectively allows and prevents the flow of fluid. For example, the valve 140 may include a channel 142 for receiving a section of tubing through which the fluid may pass. During installation of the disposable set (discussed in greater detail below), the user/technician can slide the tubing into the channel 142. In some embodiments, the valve 140 may be an automated valve that is in communication with the components within the first section 120 of the housing 110. As discussed in greater detail below, if automated, the operation of the valve 140 may be controlled by a microcontroller within the system 100 or within a blood processing system/device.

Figure 2A:
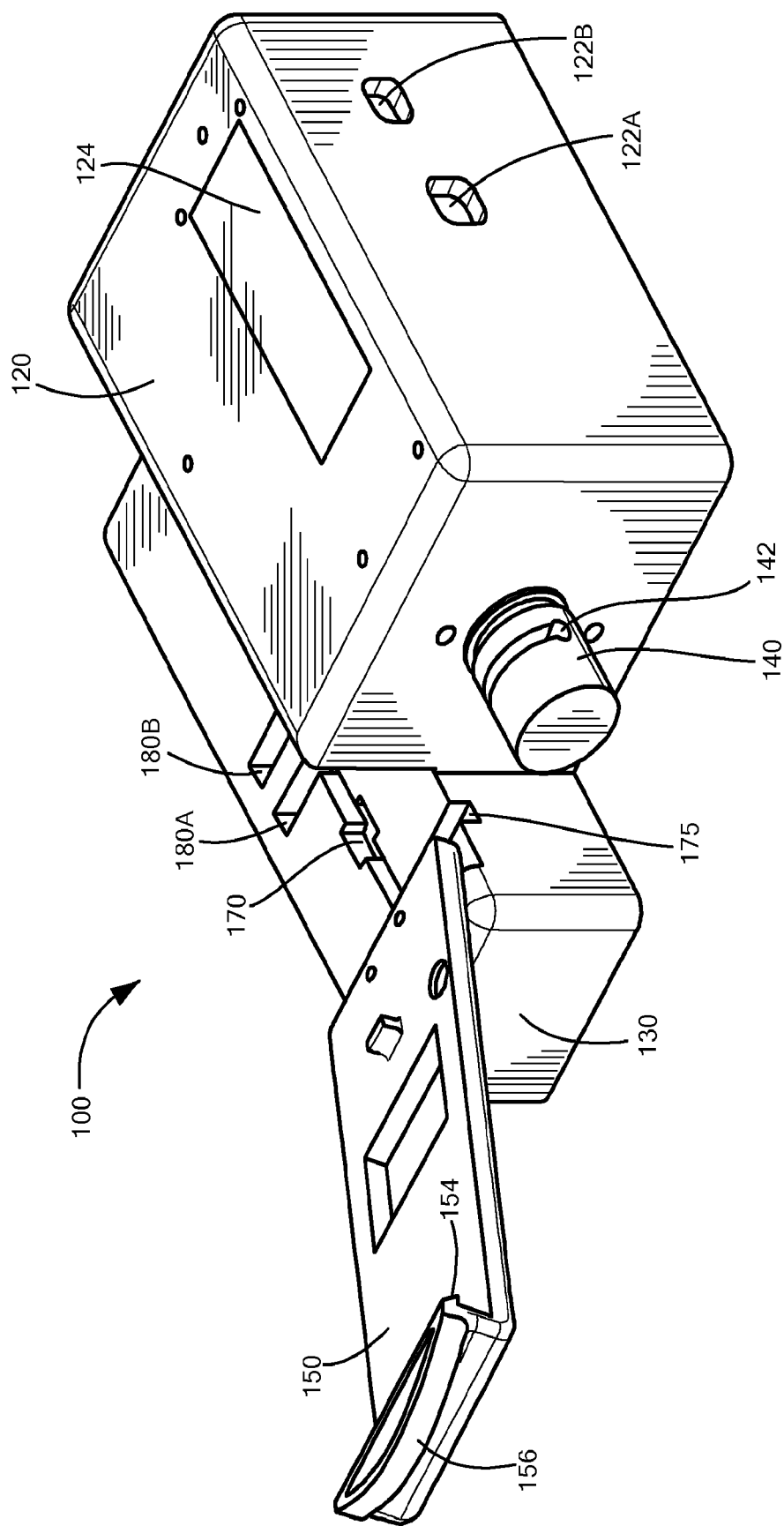
FIG. 2A schematically shows a perspective view of the fluid type detection system of FIG. 1A with the door open, in accordance with some embodiments of the present invention.
Figure 2B:
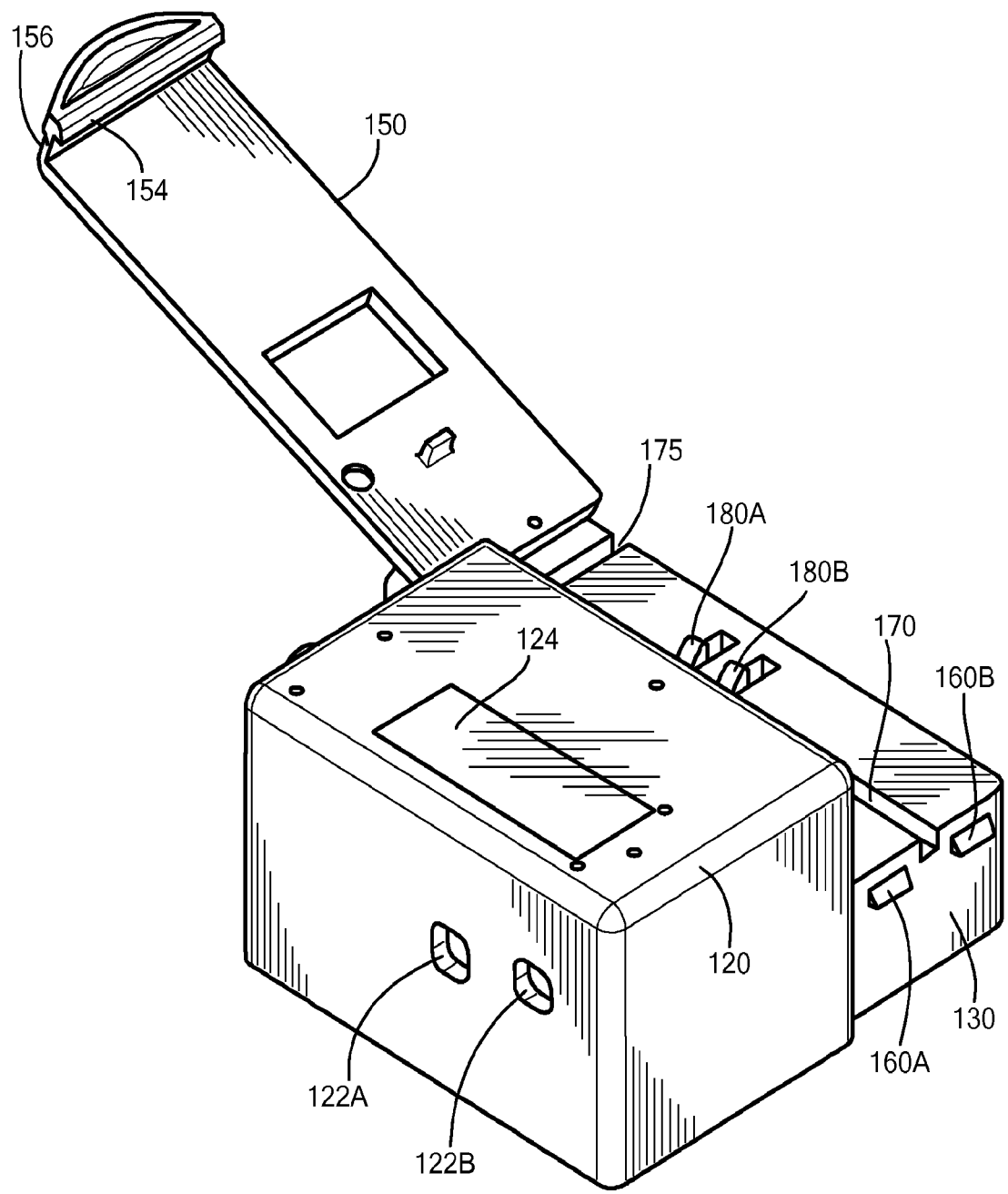
FIG. 2B schematically shows an alternative perspective view of the fluid type detection system of FIG. 1A with the door open, in accordance with some embodiments of the present invention.
Figure 2C:
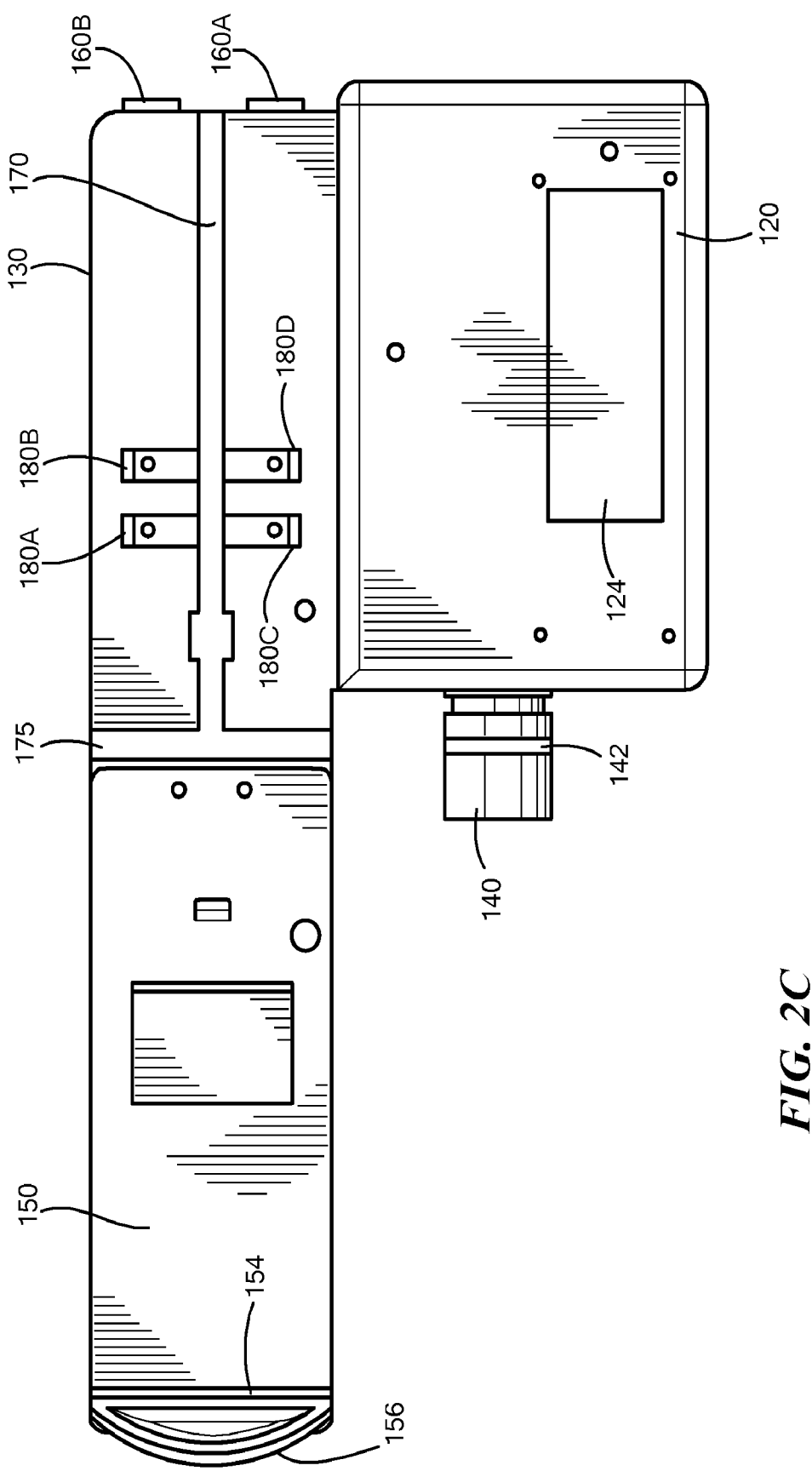
FIG. 2C schematically shows a top view of the fluid type detection system of FIG. 1A with the door open, in accordance with some embodiments of the present invention.
Figure 2D:
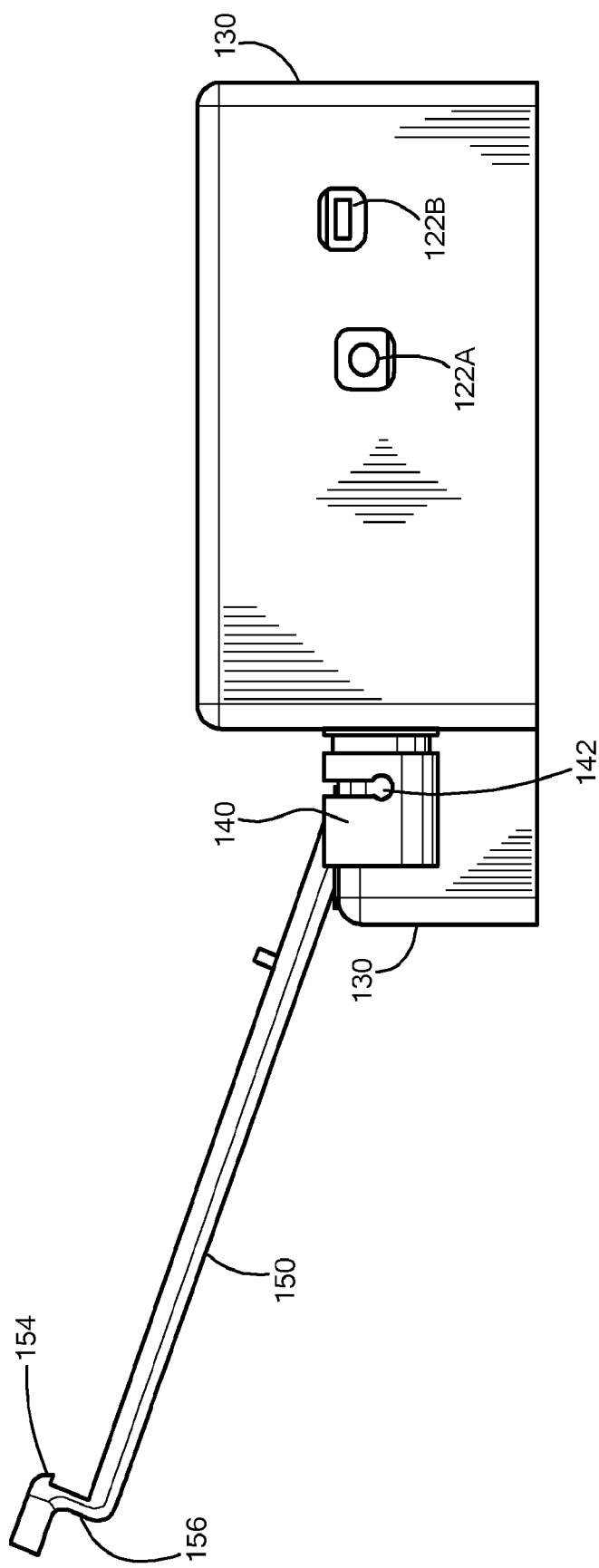
FIG. 2D schematically shows a side view of the fluid type detection system of FIG. 1A with the door open, in accordance with some embodiments of the present invention.

In addition to the first portion 120, the housing 110 also includes a second portion 130 in which a disposable set 300 (FIG. 3) may be installed. The second portion 130 may include a first channel 175 (e.g., a vertical channel) into which a section of tubing within the disposable set 300 can be installed. Additionally, the second portion 130 includes a door 150 connected to the housing 110 via a hinge 152 that allows the door 150 to open and close as needed. To ensure that the door 150 does not inadvertently open, the second portion 130 of the housing 110 may include tabs 160A/B (FIGS. 2B and 2C) that engage a lip 154 on the door 150. In such embodiments, to open the door 150, the user/technician may pull upwards on an end wall 156 of the door 150 to disengage the tabs 160A/B and lip 154. The user/technician may then lift the door 150 to open it.

Although the latching mechanism for the door 150 is discussed above as being a tab 160A/B and lip 154 configuration, it should be noted that other latching and/or locking mechanisms may be used to keep the door 150 closed. For example, the lip 154 may be located on the housing 110, and the tabs 160A/B may be located on the door 150. Additionally or alternatively, one of the components (e.g., the door 150 and/or housing 110) may include a groove and the other component may include a bump/ridge or similar structure. Furthermore, the latching mechanism can be a lock and key type system or other system suitable for keeping the door 150 closed.

As best shown in FIGS. 2A to 2D, within the interior of the second portion 130 of the housing 110 (e.g., under the door 150), the system 100 can have a second channel 170 (e.g., a horizontal channel) that extends perpendicularly from the first channel 175. The system 100 can also have a number of electrical contacts 180A-D (e.g., battery contacts) along the length of the second channel 170. As discussed in greater detail below, the electrical contacts 180A-D contact electrodes 364/366 on the disposable set 300 and are used to apply the voltage across the electrodes 364/366 and/or fluid within disposable set.

It is important to note that, although FIGS. 2A to 2D show the system 100 having four electrical contacts 180A-D, for any given disposable set, the number of contacts required/used will depend upon the number of electrodes within the disposable set 300. For example, if the set 300 only has two electrodes 364/366 (FIG. 3), the system 100 will likewise only require two contacts 180. Additionally, the configuration of the contacts 180A-D may be dependent upon the configuration of the electrodes 364/366. For example, if the electrodes 364/366 are located on the same side of the fluid flow, the system 100 may only include (or only use) contacts 180A and 180B (or battery contacts 180C and 180D). Alternatively, if the electrodes 364/366 are on opposite sides of the fluid flow, the system 100 may include only (or use only) one battery contact on either side of the fluid flow (e.g., contacts 180A and 180C, contacts 180B and 180D, contacts 180A and 180D, or contacts 180B and 180C).

Figure 3:
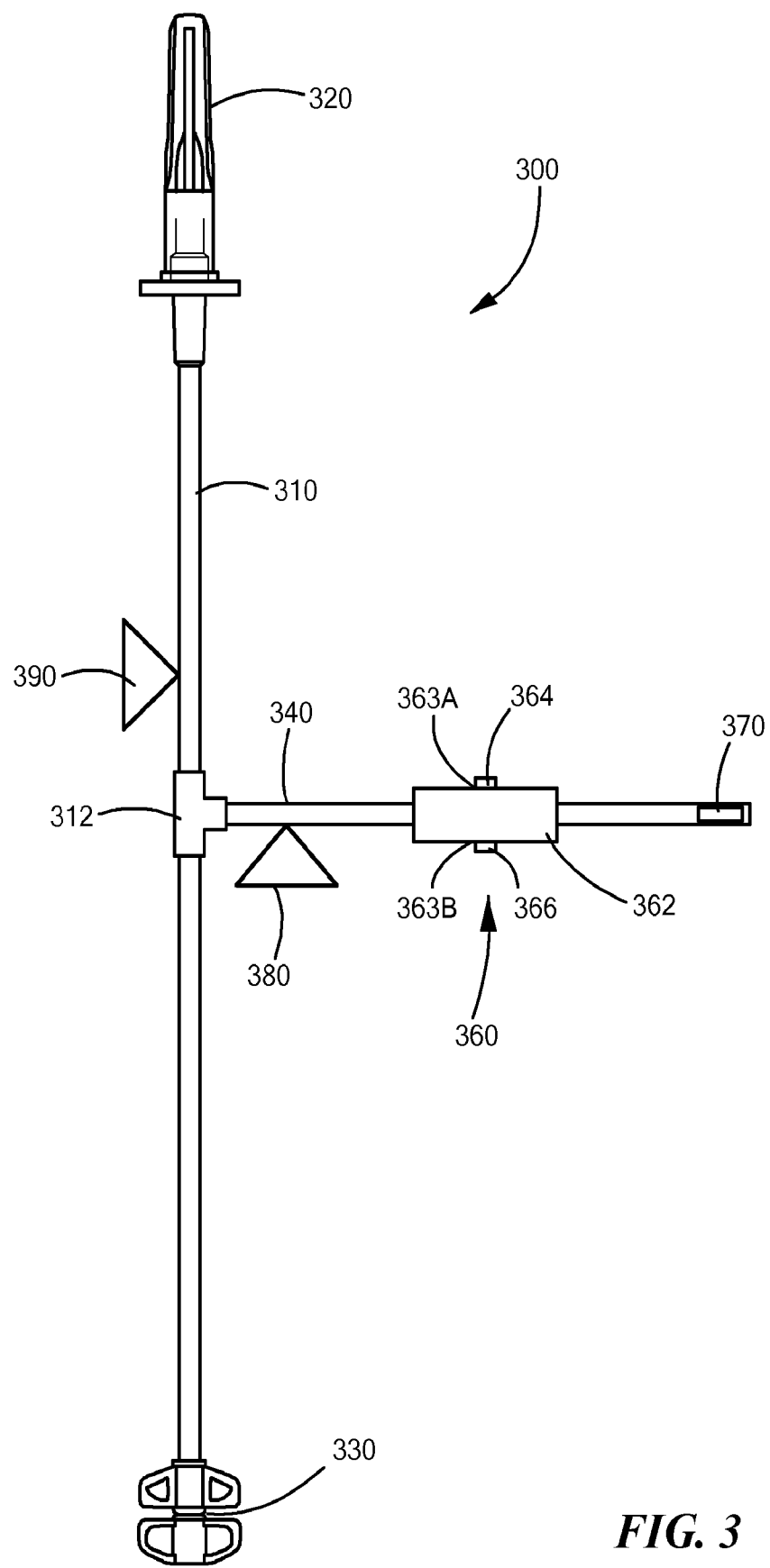
FIG. 3 schematically shows an exemplary disposable set for use with the fluid type detection system of FIG. 1A, in accordance with embodiments of the present invention.

As mentioned above, the system 100 may be used in conjunction with a disposable set 300 to determine the type of fluid flowing to/through the blood processing system (e.g., through the disposable set 300). FIG. 3 shows one embodiment of a disposable set 300 that may be used within the system 100 described above. In particular, the disposable set 300 includes a first connector 320 (e.g., a spike) that may be connected to a fluid source (e.g., a saline bag or anticoagulant bag), and second connector (e.g., a spike port or similar connector) that connects to a second disposable set installed within the blood processing system, to the blood processing system itself, and/or to a port located on a blood component separation device within the blood processing system. The disposable set 300 also has a first section of tubing 310 that connects the first connector 320 and the second connector 330 to allow fluid to flow through the set 300.

Figure 4:
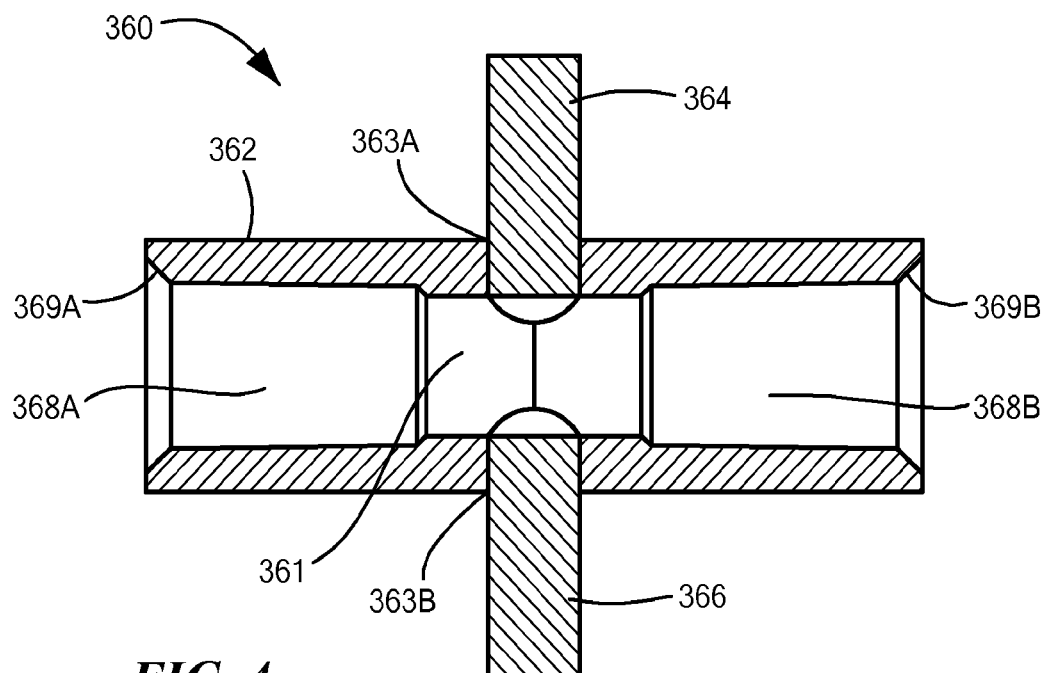
FIG. 4 schematically shows a cross-sectional view of the electrode unit within the disposable set shown in FIG. 3, in accordance with various embodiments of the present invention.

In order to apply a voltage across the fluid passing through the disposable set 300 (e.g., the first tube 310), the disposable set 300 also includes an electrode unit 360. As best shown in FIG. 4, the electrode unit 360 contains an electrode housing 362 (e.g., a plastic housing) in which the electrodes 364/366 (spaced approximately 1 inch or less apart) may be located. For example, the electrode housing 362 may include two or more openings 363A/B that extend through the wall of the housing 362 and into a flow path 361 through the electrode housing 362. The electrodes 364/366 may be press-fit into the openings 363A/B within the electrode housing 362 (or otherwise secured in the openings 363A/B) such that they are in contact with fluid in the disposable set 300, and a portion of the electrodes 364/366 extends out of the housing 362 (e.g., so that they may be connected/mated to the contacts 180A-D discussed above). The portion of the electrodes 364/366 that is exposed to the fluid may be relatively small (e.g., approximately 0.01 inches$^2$ or less).

Additionally or alternatively, the electrode unit 360 may include a septum (e.g., a polyisoprene septum; not shown) located within the openings 363A/B. In such embodiments, the septum may have a slit or similar normally closed aperture into which the electrodes 364/366 may be inserted. This, in turn, may create a seal between the septum material and the electrode 364/366 to prevent fluid and/or air from leaking past the electrodes 364/366. The electrodes 364/366 can be made from any number of materials including, but not limited to stainless steel, galvanized steel, copper, aluminum, brass, and tin coated copper. In a preferred embodiment, the electrodes 364/366 are aluminum.

To facilitate connection with the tubing in the disposable set 300 (e.g., the first tube 310 and/or the second tube 340 discussed in greater detail below) each end of the flow path 361 may be bored out to create a larger diameter and, perhaps tapered, portion 368A/B to accommodate the tubing (e.g., 0.120 inch inner diameter×0.170 inch outer diameter tubing). In this manner, the tubing may be inserted into the larger/tapered diameter portions 368A/B and secured to the unit 360 (e.g., via ultrasonically welding, solvent bonding, gluing, etc.) without reducing the effective diameter of the flow path 361 (e.g., so there is a constant diameter flow path 361 through the electrode unit 360). To that end, the increase in diameter between the larger diameter portions 368A/368B and the rest of the flow path 361 may be equivalent to the thickness of the tubing. In some embodiments, the electrode housing may include a chamfer 369A/B to allow the tubing to be more easily inserted into the larger diameter portions 368A/368B.

Figure 5A:
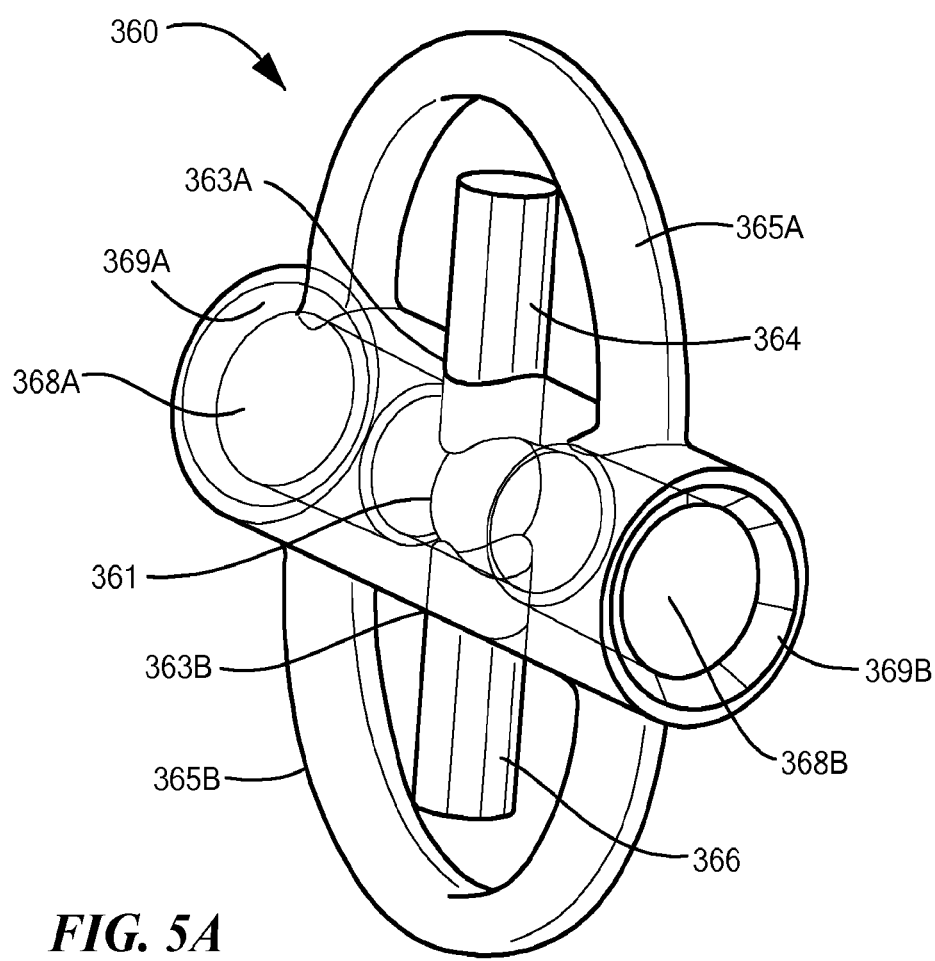
FIG. 5A schematically shows a perspective view of an alternative electrode unit, in accordance with additional embodiments of the present invention.
Figure 5C:
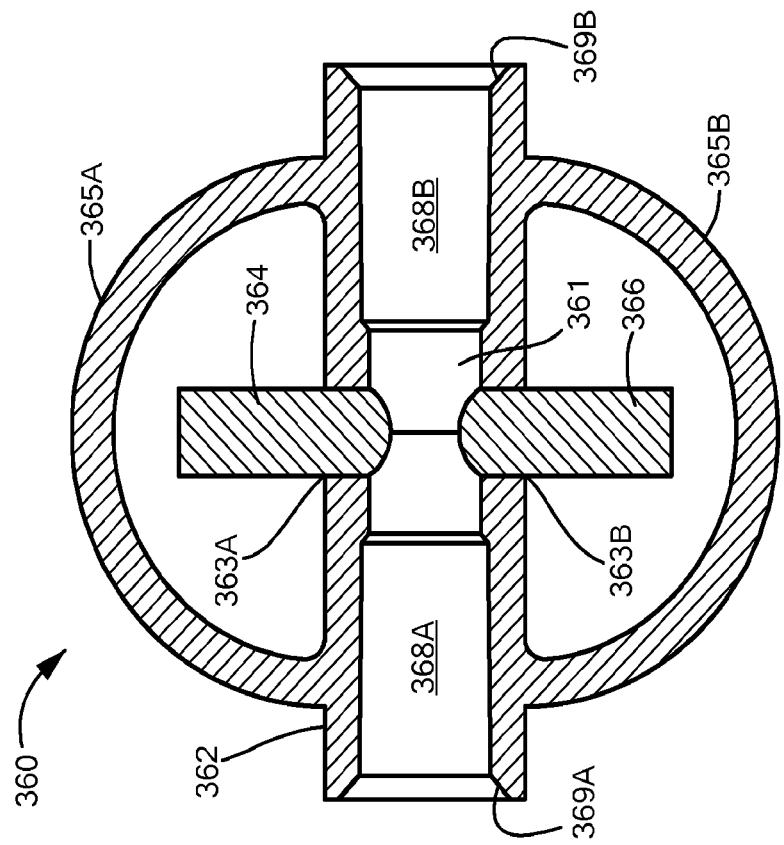
FIG. 5C schematically shows a cross-sectional view of the electrode unit shown in FIG. 5A, in accordance with some embodiments of the present invention.
Figure 5B:
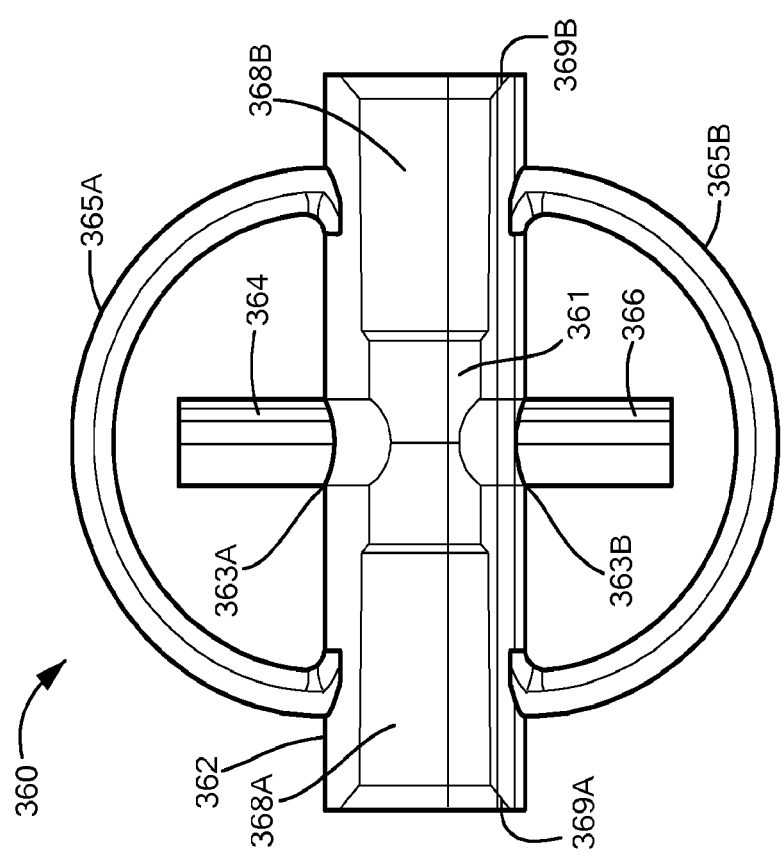
FIG. 5B schematically shows a side view of the electrode unit shown in FIG. 5A, in accordance with some embodiments of the present invention.

Although FIG. 4 shows an electrode unit 360 having a smooth cylindrical body (e.g., with the exception of the electrodes 364/366 protruding from the electrode housing 362), other embodiments of the electrode unit 360 may have additional features that help the user grasp/manipulate the electrode unit 360 (and, therefore, the disposable set 300) and protect the electrodes 364/366. For example, as shown in FIGS. 5A-5C, the electrode unit 360 may include grasping structures 365A/B (e.g., a handle) that extend from the housing 362 and over the electrodes 364/366. In addition to providing the user a place to grasp the electrode unit 360, because the grasping structures 365A/B extend over the electrodes 364/366, they also serve to protect the electrodes 364/366. For example, the grasping structures 365A/B protect the electrodes 364/366 from accidentally being knocked/pulled out of the electrode unit 360 (e.g., out of the openings 363A/B) and/or pushed further into the openings 363A/B and into the flow path 361.

Figure 6A:
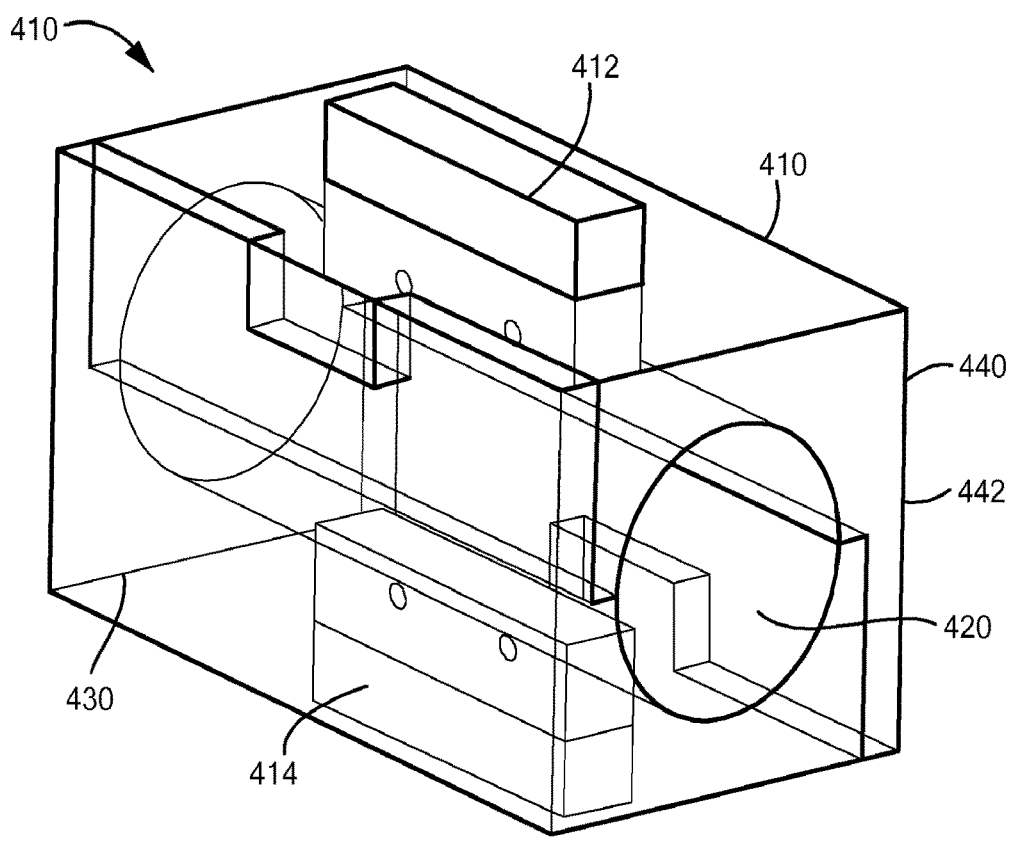
FIGS. 6A and 6B schematically show perspective views of an additional alternative embodiment of an electrode unit, in accordance with additional embodiments of the present invention.

It is important to note that, although the electrode unit 360 discussed above and shown in FIGS. 4 and 5A-5C has a single piece cylindrical body (e.g., housing 362), other embodiments of the electrode unit 360 may have different configurations. For example, as shown in FIG. 6A, the electrode unit 360 may have rectangular-shaped (or square-shaped) housing 410. Similarly, the electrodes 412/414 may also be rectangular in shape (e.g., as opposed to cylindrical) and the electrodes 412/414 may extend along a portion of the length of the flow path 420.

Figure 6B:
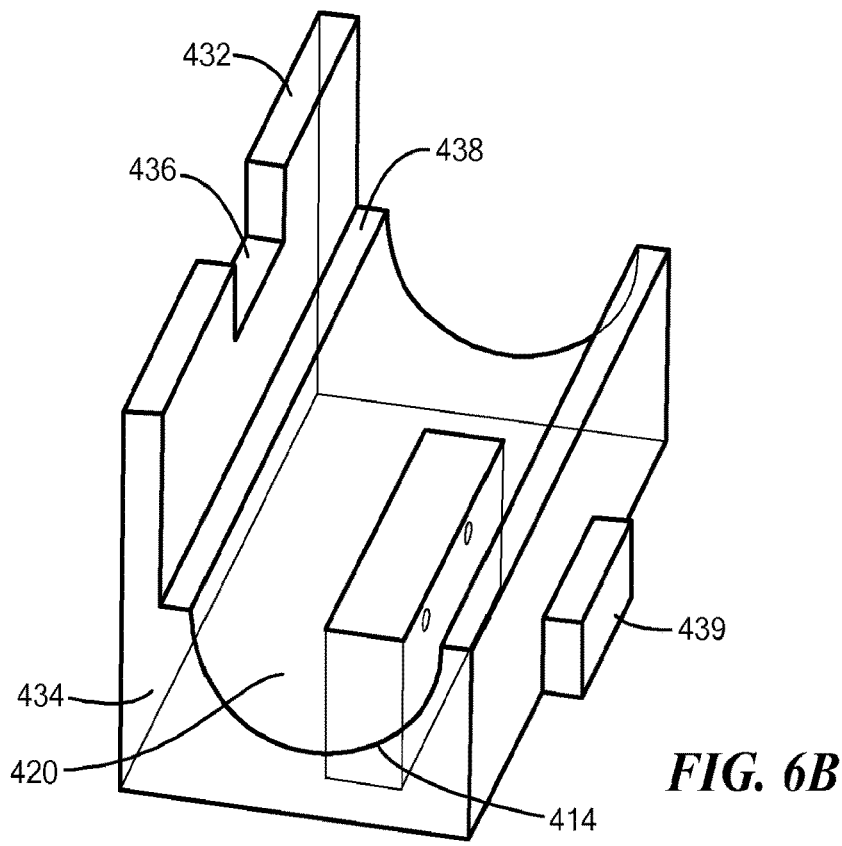

Additionally, the housing 410 (or housing 362) may include two portions—a first portion 430 and a second portion 440—that may be secured together (discussed in greater detail below) to form the housing 410. To ensure the proper alignment of the first and second portion 430/440 of the housing 410, each portion 430/440 can have various alignment features. For example, each portion (portion 430 in FIG. 6B) may have a wall 432 that extends from a body 434 that, in turn, defines part of the fluid path 420 through the housing. The wall 432 may include a notch 436 or indent near the top, and the body 434 can include a shelf 438 at the base of the wall 432 and a protrusion 439 extending from the other side (e.g., the side without the wall 432). It should be noted that, although FIG. 6B shows only one portion 430 of the housing 410, the other portion 440 can have similar features.

During assembly of the electrode unit 410, the user/technician may place the first portion 430 onto the second portion 440 such that the end of the wall 432 on one portion (e.g., first portion 430) contacts the shelf portion 438 on the other. Additionally, when the two portions 430/440 are in place, the protrusion 439 on one portion will enter the notch 436 on the other portion to align the two portions 430/440 of the housing 410 and the flow path 420. As discussed in greater detail below, the portions 430/440 may then be secured to one another (e.g., via ultrasonically welding, solvent bonding, gluing, etc.).

Figure 7A:
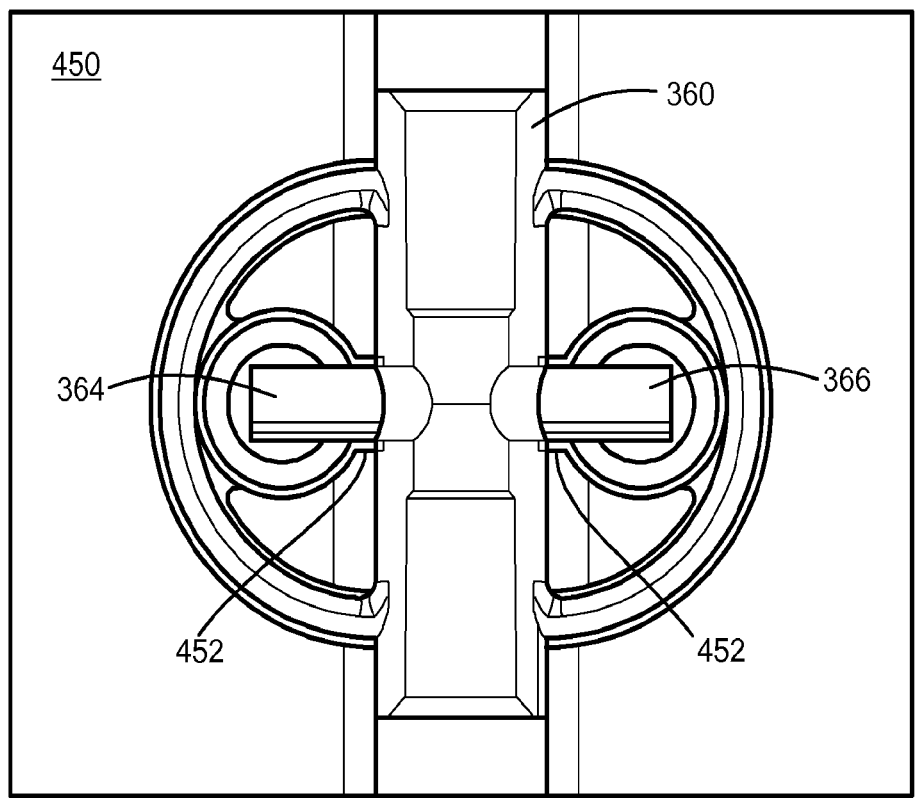
FIGS. 7A and 7B schematically show a mold for manufacturing the electrode unit shown in FIG. 5A, in accordance with embodiments of the present invention.
Figure 7B:
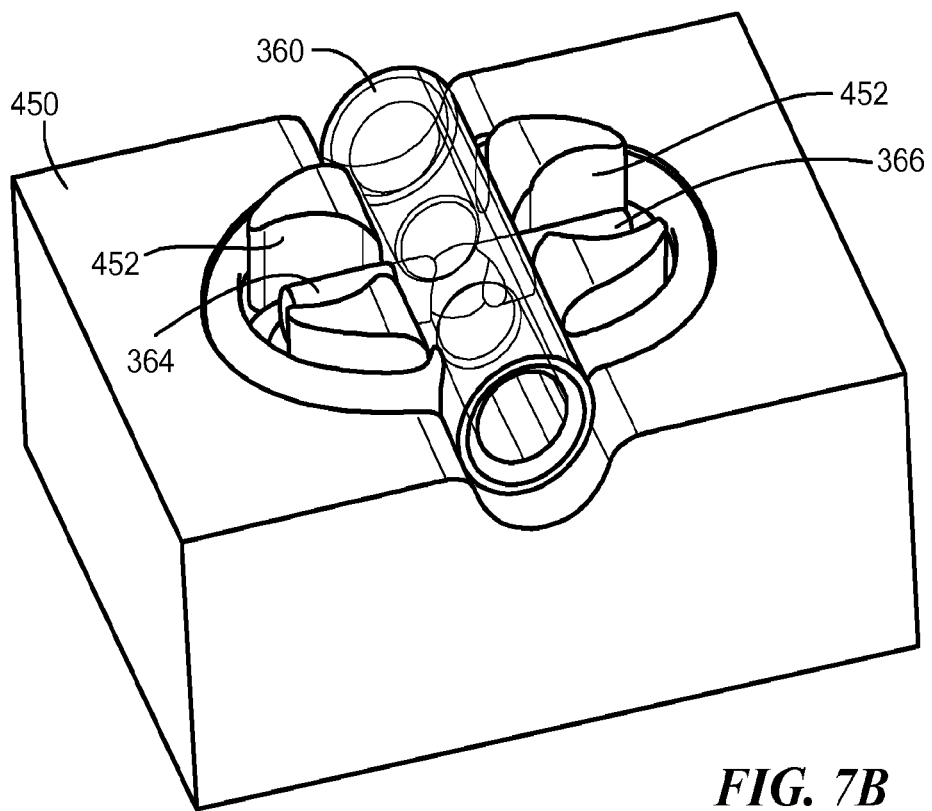

It should be noted that the electrode units 360/410 discussed above can be manufactured using any number of manufacturing methods. For example, the electrode unit (e.g., electrode unit 360) may be injection molded as a single unit with the electrodes 364/366 in place. In particular, as shown in FIGS. 7A and 7B, the mold 450 for the injection molding process may include recesses 452 for holding the electrodes 364/366. The housing 362 of the electrode unit 360 may then be molded around the electrodes 364/366 such that the injection molding process yields a complete electrode unit 360 with electrodes 364/366. Alternatively, the housing 362 of the electrode unit 360 may be molded with the opening 363A/B for the electrodes 364/366, and the electrodes 364/366 may be inserted after molding (e.g., via press-fit directly into the holes 363A/B or into the septum discussed above).

For embodiments having multi-part housings (e.g., like housing 410 that includes the first portion 420 and the second portion 430), each portion of the housing may be injection molded in a manner similar to that described above. In particular, each portion 420/430 may be injected molded with the electrodes 412/414 in place or with just openings for the electrodes 412/414 (with the electrodes 412/414 being inserted/installed after). The two portions 420/430 of the housing 410 may then be assembled, as discussed above, to form the housing 410 (e.g., by gluing, solvent bonding, ultrasonically welding, etc.).

In some instances, it may be desirable to isolate the fluid that comes into contact with the electrodes 364/366. For example, the voltage that is applied across the fluid via the electrodes 364/366 can create a chemical reaction at the electrodes 364/366 that may, in turn, change the properties of the liquid. To that end, the disposable set 300 may include a second tube 340 extending from the first tube 310 (e.g., via a Y-connector, T-connector 312, etc.), and the electrode unit 360 may be located within the second tube 340. To facilitate fluid flow into the second tube 340, the second tube 340 may also include a ventilation plug 370 (e.g., a Porex plug) located at an end of the tube 340. The ventilation plug 370 allows air within the second tube 340 to exit as the second tube 340 begins to fill with fluid. Once the fluid reaches the plug 370, the plug 370 may seal itself to prevent the fluid from leaking out of the disposable set 300.

To prevent the fluid within the second tube 340 from re-entering the first tube 310 (and flowing into the blood processing system), the disposable set 300 may include a valve 380 located on the second tube 340. The valve 380 may be a manual valve or an automated valve. For example, if the valve 380 is a manual valve, the user may close the valve 380 when the second tube 340 fills with fluid. Alternatively, if the valve 380 is an automated valve, the system 100 (or the blood component separation system) may automatically close the valve 380 when the second tube 340 is full (or when a line sensor within the blood processing system detects the presence of fluid).

Figure 8A:
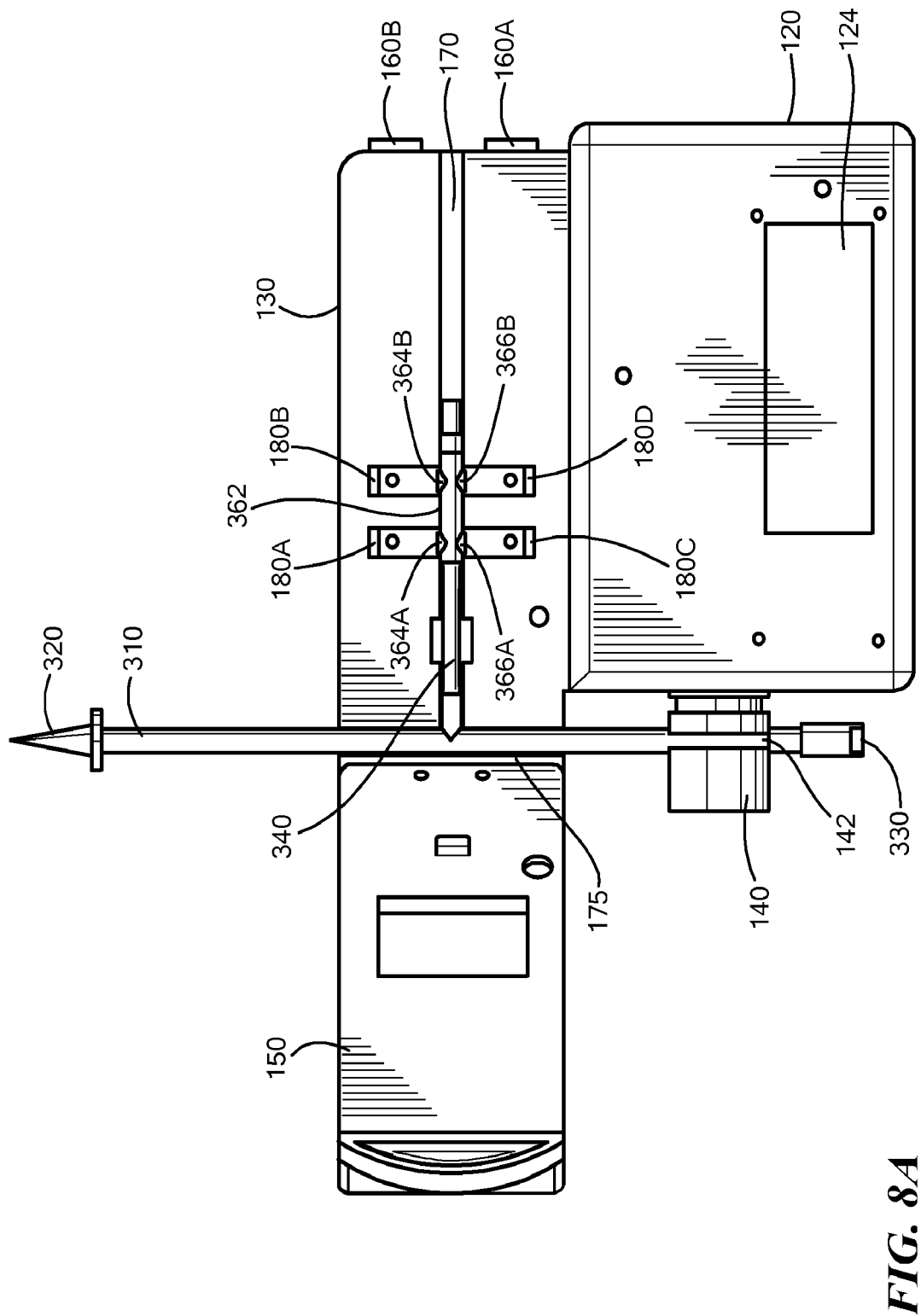
FIG. 8A schematically shows a top view of the fluid type detection system of FIG. 1A with the door open and disposable set installed, in accordance with some embodiments of the present invention.
Figure 8B:
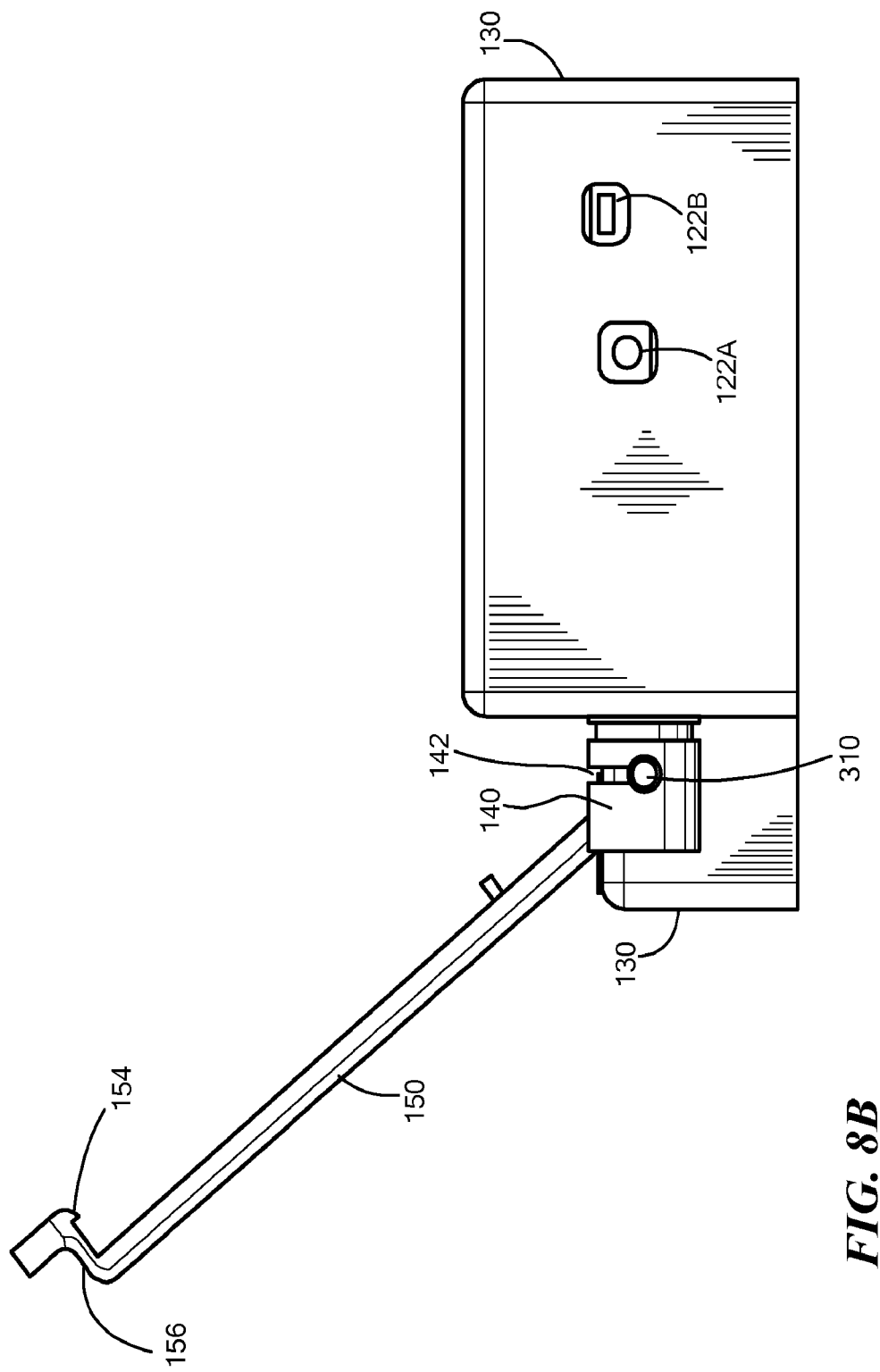
FIG. 8B schematically shows a side view of the fluid type detection system of FIG. 1A with the door open and disposable set installed, in accordance with some embodiments of the present invention.
Figure 8C:
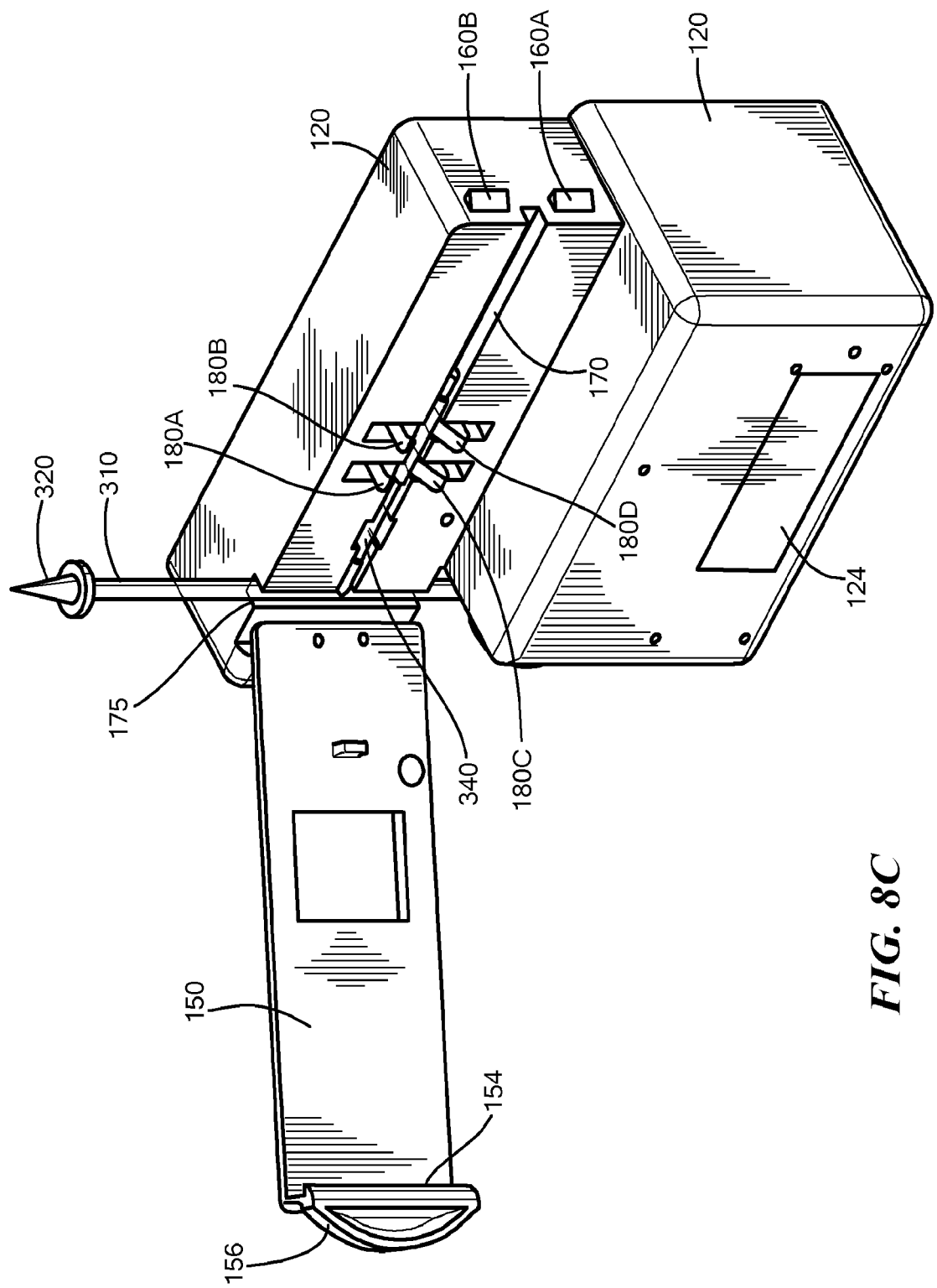
FIG. 8C schematically shows a perspective view of the fluid type detection system of FIG. 1A with the door open and disposable set installed, in accordance with some embodiments of the present invention.
Figure 9A:
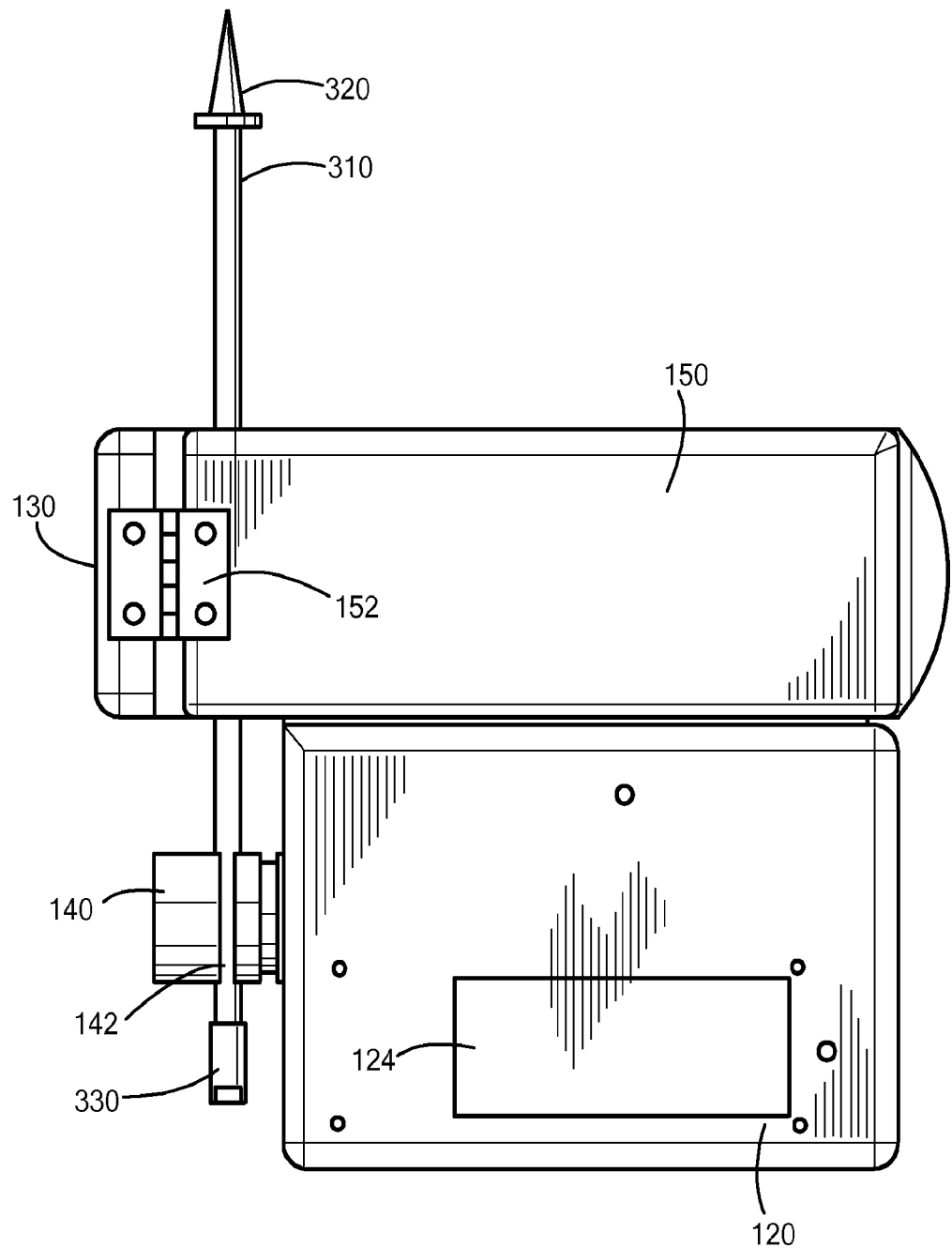
FIG. 9A schematically shows a top view of the fluid type detection system of FIG. 1A with the door closed and disposable set installed, in accordance with some embodiments of the present invention.
Figure 9B:
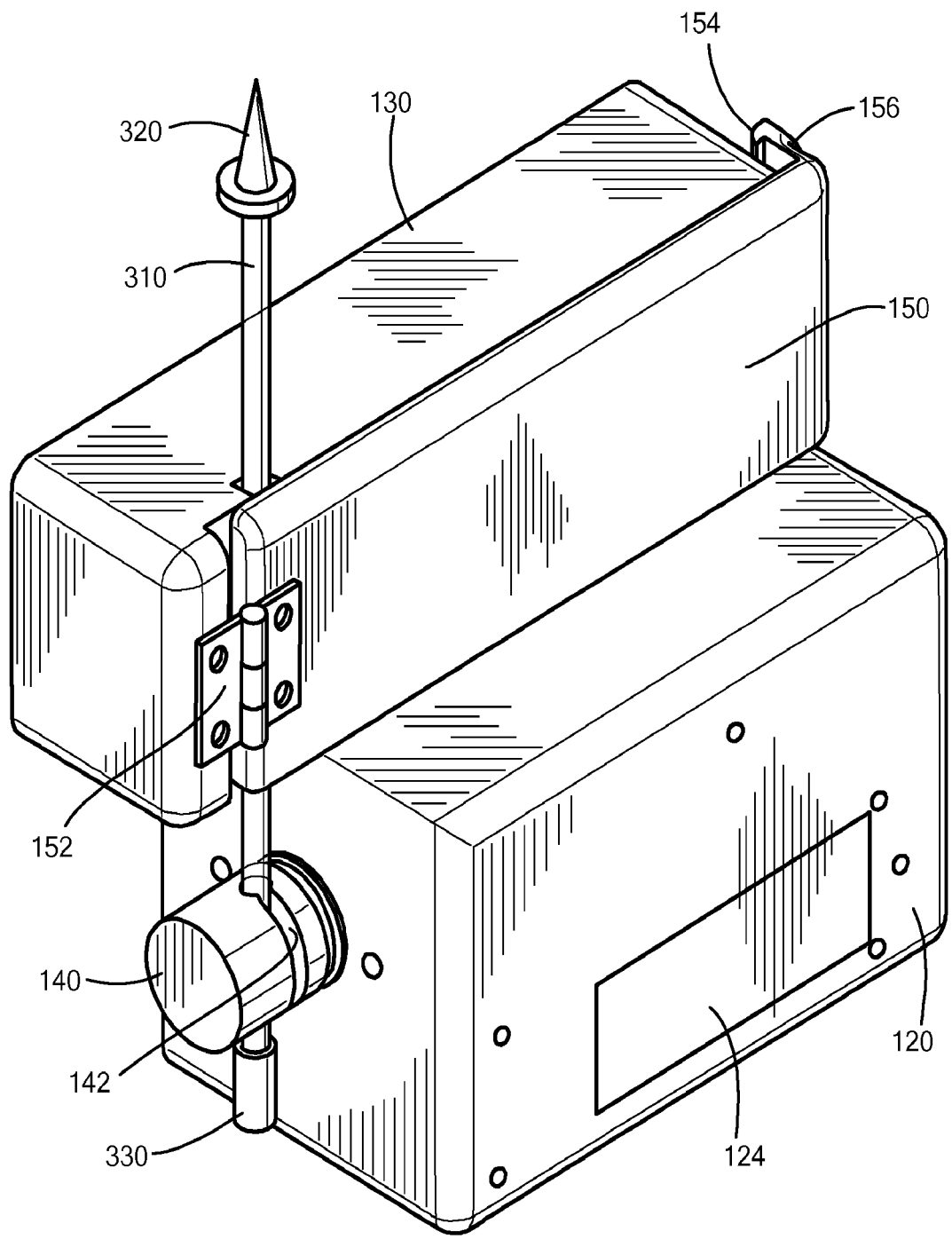
FIG. 9B schematically shows a perspective view of the fluid type detection system of FIG. 1A with the door closed and disposable set installed, in accordance with some embodiments of the present invention.
Figure 9C:
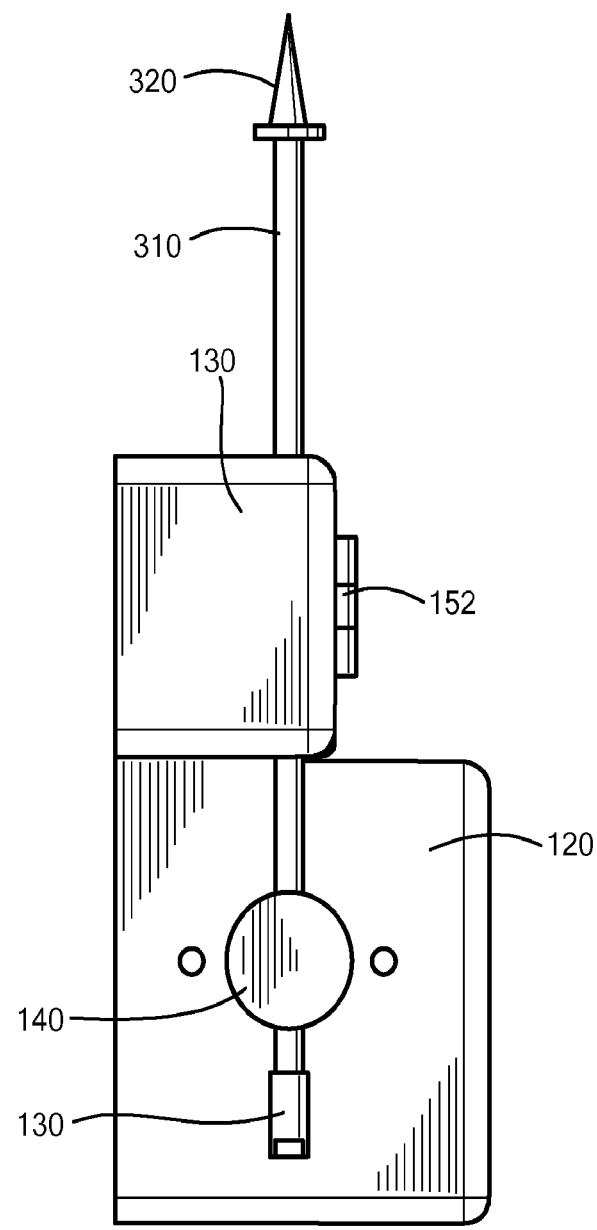
FIG. 9C schematically shows a side view of the fluid type detection system of FIG. 1A with the door closed and disposable set installed, in accordance with some embodiments of the present invention.

As mentioned above, the disposable set 300 may be installed into the detection system 100. To that end, during set-up of the blood processing system, the user/technician may install the disposable set 300 into the detection system 100 (e.g., into the first and second sections 120/130 of the housing 110). For example, as shown in FIGS. 8A-8C, the user/technician may first unlatch and open the door 150 of the second section 130. The user/technician may then insert the first tube 310 into the channel 142 in the valve 140 and the first channel 175 (e.g., the vertical channel) of the second portion 130 of the housing 110. Additionally, the user/technician may insert the second tube 340 into the second channel 170 (e.g., the horizontal channel) such that each of the electrodes 364/366 in the electrode unit 360 are in contact with an electrical contact 180A-D. Once the first tube 310 and the second tube 340 are in the respective channels 170/175 and the electrodes 364/366 are in contact with battery contacts 180A-D, the user/technician may close and latch the door 150 (FIG. 9A-9C).

Figure 10:
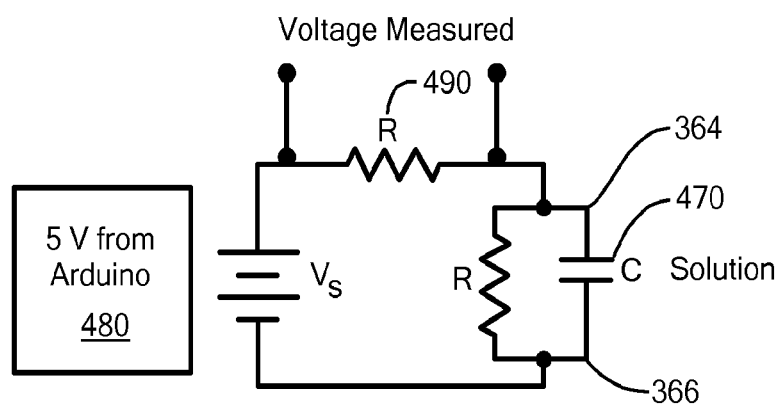
FIG. 10 schematically shows a circuit diagram for the fluid type detection system of FIG. 1A, in accordance with some embodiments of the present invention.

Once the disposable set 300 is installed into the detection system 100, the second connector 330 is connected to the blood processing device, and the first connector 320 is connected to the fluid source, the detection system 100 is ready for operation. To that end, as fluid begins to flow from the fluid source, a portion of the fluid will enter the second tube 340, were it comes into contact with the electrodes 364/366. The detection system 100 may then apply a voltage to the electrodes 364/366 and measure a voltage drop. For example, as shown in FIG. 10 (which shows an exemplary circuit diagram for the detection system 100), the solution in the second tube 340 acts as a capacitor 470 and resistor in parallel. A microcontroller 480 (or other voltage source)

may then apply a voltage across the electrodes 364/366. The microcontroller 480 (or other voltage detector) may then measure the voltage drop across a resistor 490 that is in series with the solution and electrodes 364/366.

As mentioned above, it has been determined that the contact between the fluid and the electrodes 364/366 may cause chemical reactions at the electrodes 364/366. These chemical reactions, in turn, create a build-up of chemicals on the electrodes and can increase the resistance to the flow of current (e.g., polarization resistance). The extent of the chemical reactions (and build-up of chemicals on the electrodes 364/366) and the resultant change in polarization resistance are different for saline and citrate based anticoagulants. By measuring the voltage drop and/or polarization resistance, the system 100 (e.g., the microcontroller 480) can determine the type of fluid within the second tube 340 (e.g., the type of fluid to which the disposable set 300 is connected).

It is important to note that, because the polarization resistance is based upon the chemical reactions that occur between the fluid and the electrode material, the change in polarization resistance may depend upon the material used for the electrodes 364/366. For example, when saline is flowing through the system 100, the polarization resistance may be lower for some electrode materials and higher for others, as compared to the polarization resistance of the citrate based anticoagulant. Therefore, some embodiments of the present invention, may take into account the electrode material when determining the type of fluid.

As mentioned above, too much anticoagulant can be very harmful to the donor. Therefore, if the system 100 detects that the fluid passing through the disposable set 300 is anticoagulant instead of saline (e.g., that the user accidentally connected the first connector 320 to a container of anticoagulant instead of a container of saline), the microcontroller 480 may generate an alarm. For example, the microcontroller 480 may generate an audible alarm (e.g., a beep) and/or may show a visible alarm on the display 124. When the alarm sounds and/or is displayed, the user/technician may then close the valve 140 to prevent the anticoagulant from reaching the donor. Alternatively, if the valve 140 is an automated valve, the system 100 (or the blood processing system) may automatically close the valve 140 when the system 100 detects anticoagulant. As shown in FIG. 3, in some embodiments, the disposable set 300 may also have a second valve 390 located upstream of the second tube 340 to help prevent the flow of fluid. Like valve 140, the second valve 390 may be a manual or an automated valve.

It should be noted that, although the embodiment described above measures the voltage drop across a resistor 490 in series with the solution, other embodiments can measure the voltage drop and/or resistance differently. For example, in some embodiments, the system 100 may not include the resistor 490. In such embodiment, the voltage drop and/or resistance may be measured directly across the electrodes 364/366. Additionally, instead of the voltage drop and/or resistance, some embodiments may measure the current across the electrodes 364/366.

Figure 11:
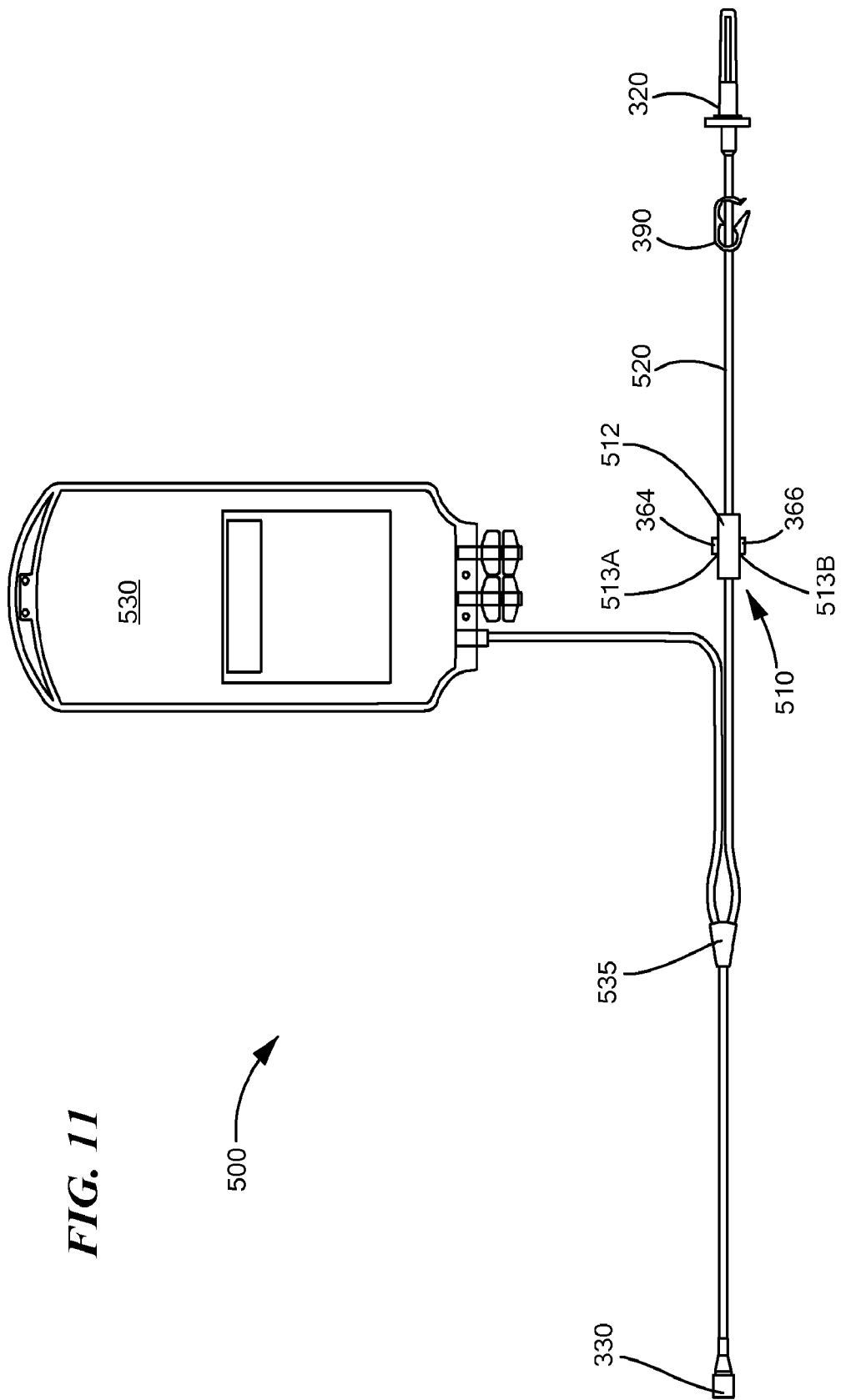
FIG. 11 schematically shows an alternative disposable set with an in-line electrode unit, in accordance with further embodiments of the present invention.

It is also important to note that, in some instances, it may not be necessary to isolate the fluid (e.g., saline or anticoagulant) that comes into contact with the electrodes. For example, in some embodiments, the chemical reactions that take place at the electrodes 364/366 may only have a very minimal impact (or no impact) on the overall quality and characteristics of the fluid. To that end, as shown in FIG. 11, some embodiments of the disposable set 500 may include an in-line electrode unit 510. Like the isolated electrode unit 360 (or unit 410) discussed above, the in-line electrode unit 510 includes a housing 512 with openings 513A/B into which the electrodes 364/366 may be press-fit (or otherwise secured). However, the electrode unit 510 may be located on the main line 520 that connects the fluid source to the blood processing device. Additionally, because there is no need to isolate the in-line disposable set 500, the in-line disposable set 500 need not have a second tube.

In such embodiments, the fluid from the fluid source (e.g., the saline container or anticoagulant container), will pass through the main line 520 and the electrode unit 510, where the system 100 will determine the type of fluid. If it is the correct type of fluid (e.g., saline), the fluid will continue to flow through the line and into the blood processing device connected to the second connector 330. If the fluid is not the correct fluid (e.g., if it is anticoagulant), the system 100 will alarm and the valve 140 will be closed (e.g., either manually by the user in response to the alarm or automatically by the system 100) to prevent the anticoagulant from reaching the donor connected to the blood processing device.

Figure 12:
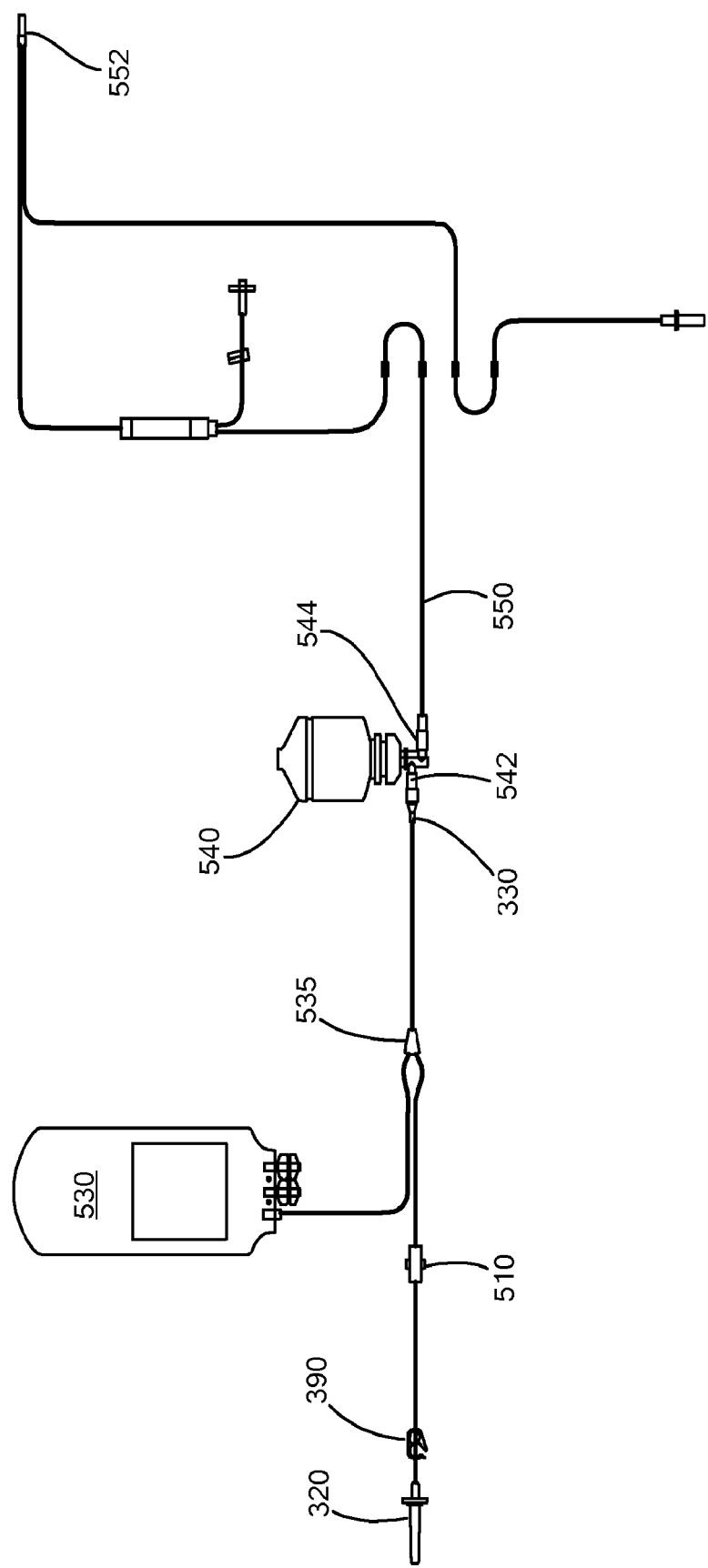
FIG. 12 schematically shows the disposable set of FIG. 11 connected to a blood component separation device, in accordance with some embodiments of the present invention.

In some embodiments, the disposable set 500 can include additional components that are used in blood processing and/or apheresis. For example, as shown in FIGS. 11 and 12, the disposable set 500 can include one or more blood component bags 530 that are fluidly connected to the main line 520 via a connector 535. As discussed in greater detail below, the blood component bag(s) 530 can be used to collect blood components (e.g., plasma) during blood processing and/or apheresis.

Like the disposable set shown in FIG. 3, as shown in FIG. 12, the in-line disposable set 500 includes a first connector 320 (e.g., a spike) that may be connected to the fluid source, and a second connector 330 that connects to a port 542 (e.g., an outlet port) on a blood component separation device 540 located within the blood processing system (or to another disposable set that, in turn, is connected to the blood processing system. The other port 544 (e.g., the inlet port) of the blood component separation device 540 may, in turn, be fluidly connected to the donor/subject via another disposable set 550 through which whole blood can be drawn from the donor/subject (via a venous access device 552) and into the blood component separation device 540.

Figure 13:
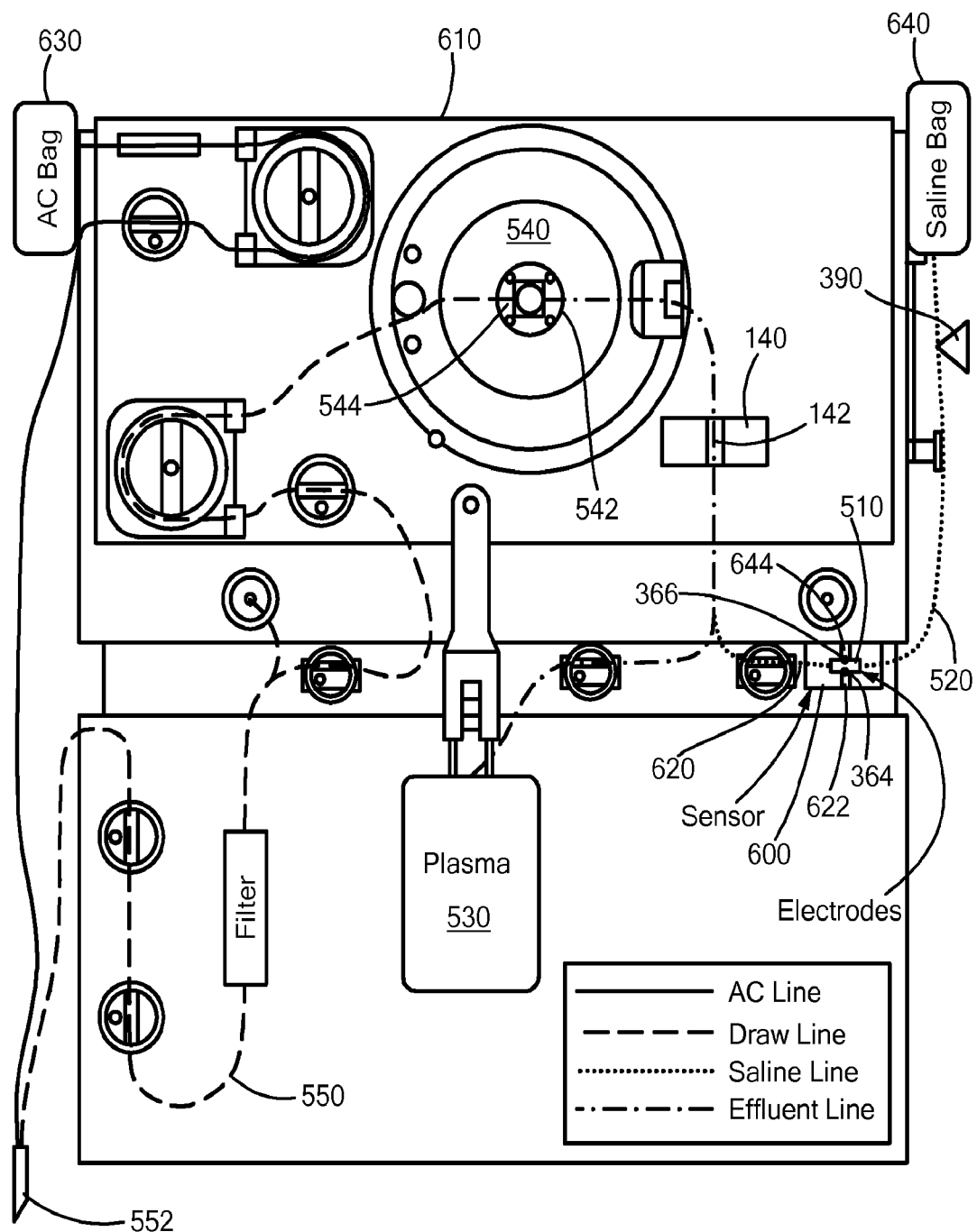
FIG. 13 schematically shows the disposable set of FIG. 11 installed in a blood processing system, in accordance with some embodiments of the present invention.

Although the embodiments discussed above and shown in FIGS. 1-10 are stand-alone systems 100 that can operate independently of the blood processing system to which they are connected, some embodiments may be incorporated directly into the blood processing systems. For example, as shown in FIG. 13, the detection system 600 may be located within the blood processing system 610. It is important to note that, in such embodiments, the detection system 600 need not have a housing with the various channels shown in FIGS. 2A-2D. Rather, if it is an in-line system like that shown in FIG. 13, the integrated detection system 600 need only have a single channel 620 into which the main line/tube 520 and the electrode unit 510 can be installed. The channel 620 may include the electrical contacts 622/624 required to apply the voltage to the electrodes 364/366, and measure the voltage drop/resistance, as discussed above.

In some embodiments, the integrated detection system 600 may include all of the components required to apply the voltage, measure the voltage drop, and determine the type of fluid (e.g., a voltage generator, voltage detector, microcontroller, display etc.). However, in other embodiments, the electrical contacts 622/624 may be connected to the power supply and/or microcontroller of the blood processing system 610. In such embodiments, the microcontroller of the blood processing system 610 may determine the type of fluid (e.g., by applying the voltage, measuring the voltage drop, etc.), and any alarms may be displayed on a display located on the blood processing system 610.

Prior to performing a blood apheresis procedure (e.g., a plasmapheresis procedure), the user/technician may install a first disposable set (e.g., disposable set 550) into the blood processing system 610 and connect the first disposable set 550 to the inlet 544 of the blood component separation device 540. The user/technician may then install the disposable set 500 with the electrode unit 510 by connecting the second connector 330 to the outlet 542 of the blood component separation device 540 and inserting the electrode unit 510 into the detection system 600. Once the disposable sets 550/500 are installed and properly connected to the blood component separation device 540, the user may then connect an anticoagulant bag 630 to the first disposable set 550, and a saline bag 640 to the first connector 320 on the fluid detection disposable set 500.

When the user/technician is ready to begin processing, the user/technician may insert the venous access device 552 into the arm of the donor/subject and begin to draw whole blood from the donor/subject and into the blood component separation device 540, where it is separated into its individual components (e.g., red blood cells, plasma, platelets, etc.). As mentioned above, because the saline bag 640 and anticoagulant bag 630 look similar, there is a risk that the user/technician may have accidentally connected the anticoagulant bag 630 to the wrong connector (e.g., they may have accidentally connected the anticoagulant bag 630 to the first connector 320 on the fluid detection disposable 500). Therefore, during the apheresis process, as the fluid from the container connected to the first connector 320 begins to flow through the main line 520, it will pass through the electrode unit 510, where the fluid detection system 600 will determine (as discussed above) whether the fluid is saline or anticoagulant.

If the detection system 600 determines that the fluid is saline (e.g., meaning that the user/technician correctly connected the fluid bags), the apheresis process will continue normally and the desired blood component (e.g., plasma) may be extracted from the blood component separation device 540 and collected in the blood component bag 530. However, if the detection system 600 determines that the fluid is anticoagulant (e.g., meaning the user/technician corrected the wrong fluid bag), the detection system 600 (or the blood processing system 610) will generate an audible and/or visible alarm. Additionally, if the valve 140 and/or valve 390 is an automated valve, the detection system 600 (or the blood processing system 610) will close the valve 140/390 to prevent the anticoagulant from reaching the blood component separation device 540 and being sent to the donor/subject.

It is important to note that although the above system is shown and described in relation to a plasmapheresis process (e.g., for the collection of plasma), this for illustration purposes only. Embodiments of the present invention can be used in any number of blood processing and apheresis procedures including, but not limited to, the collection of red blood cells, the collection of platelet, blood washing and/or blood salvage procedures, etc. Additionally, although the fluid determination process is described as taking place after the donor is connected to the blood processing system and during the apheresis process, in some embodiments, the determination process can happen earlier. For example, in some embodiments, the test to determine the type of fluid can occur before the donor is connected and/or during a prime sequence.

Figure 14:
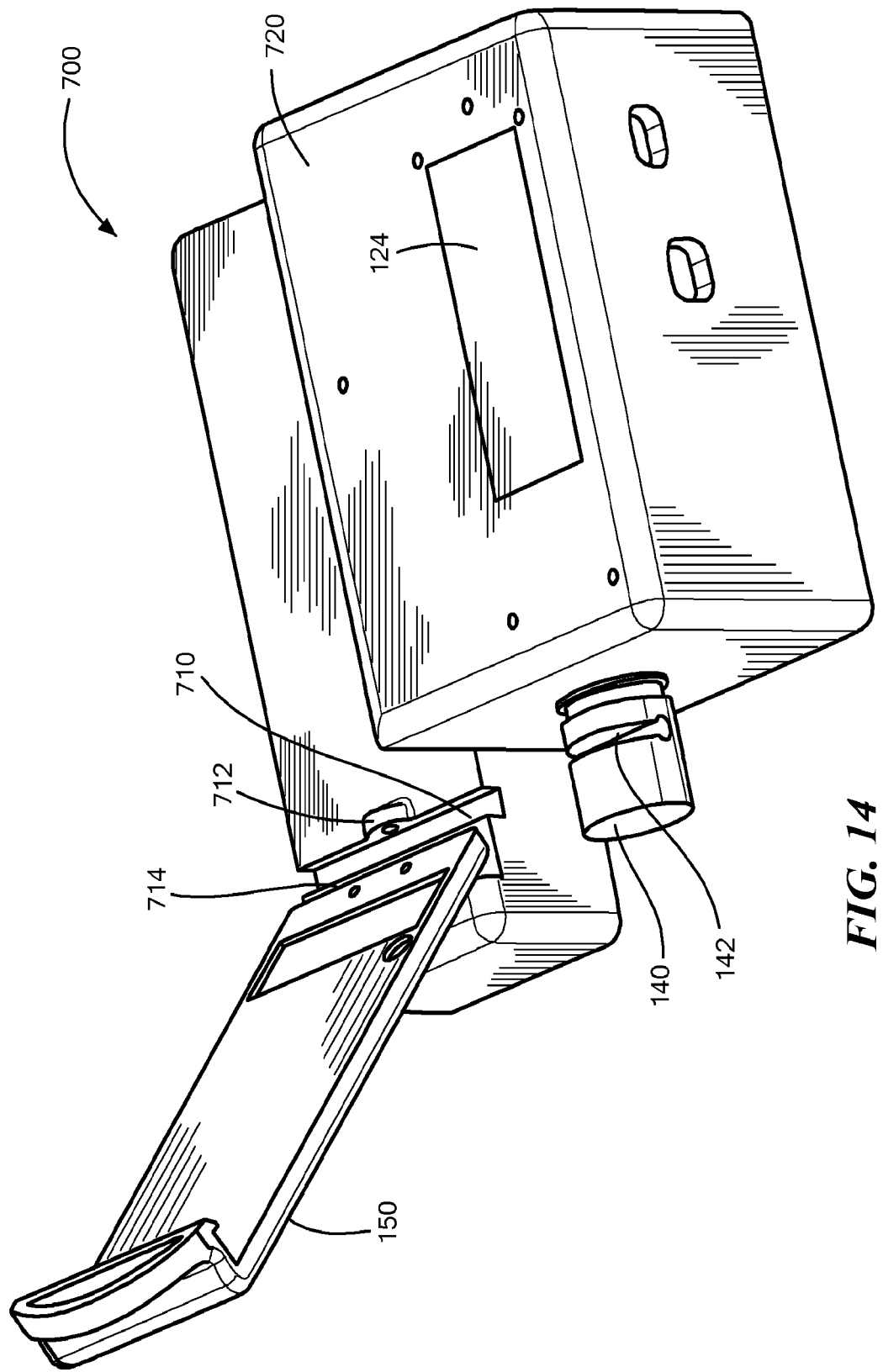
FIG. 14 schematically shows an alternative fluid type detection system in accordance with additional embodiments of the present invention.

Although the above described embodiments determine the type of fluid by applying a voltage and measuring a voltage drop, as shown in FIG. 14, other embodiments may utilize ultra-violet ("UV") light to determine the type of fluid. In such embodiments, the fluid type detection system may include a UV light source/emitter 712 (approximately 200-240 nm) located on one side of the fluid flow (e.g., on one side of the fluid line), and a UV light detector/receiver 714 located on an opposing side of the fluid flow. For example, like the embodiment shown in FIGS. 1A-1C, the fluid detection system 700 shown in FIG. 14 can include a channel 710 into which the tubing leading from the fluid source can be inserted. The UV light source 712 can be located on one side of the channel and the UV detector 714 can be located on the opposite side of the channel 710. Both the UV light source/emitter 712 and the UV detector/receiver 714 may be in communication with electronics (e.g., a microcontroller) within the housing 720 or the blood processing device (e.g., if integrated with the blood processing device).

In operation, as the fluid passes through the tubing of the disposable set and towards the blood processing device 610 (e.g., towards the blood component separation device 540), the UV light will shine through the tubing and fluid, and the UV detector/receiver 714 will measure the amount of UV transmission through the fluid. Based upon the amount of UV transmission, the system 700 (e.g., the microcontroller) can determine the optical density (a measurement of the absorbance) of the fluid. Furthermore, because the optical density of saline is significantly less than that of anticoagulant (e.g., at a UV wavelength of approximately 200-240 nm), the system 700 is able to determine whether the fluid within the line is saline or anticoagulant.

Furthermore, like the embodiments discussed above, the system 700 may then generate an audible and/or visible alarm if the system 700 determines the fluid to be anticoagulant. This alarm, in turn, will alert the user/technician of the issue and notify the user/technician to stop the blood processing device (or close a valve to prevent additional fluid to flow from the anticoagulant source). Alternatively, if the valve (e.g., valve 140) is automated and the detection system 700 is in electrical communication with or integrated with the blood processing system 610, the detection system 700 may close the valve 140 and/or stop the blood processing system 610.

It should be noted that, although the above embodiment is described as using a UV light source with a wavelength of approximately 200-240 nm, the wavelength can be varied depending upon the application (e.g., the type of fluids being tested, the type of anticoagulant used, etc.). Furthermore, because the accuracy of the detection system 700 relies on the accurate measurement of the transmission through the fluid, the section of tubing through which the UV light shines must be UV transparent at the wavelength of the UV light source/emitter 712. For example, the tubing may have a window (or similar area) that is made from a UV transparent material such as Quartz (which is transparent across a relatively large UV range) on both sides of the tubing. These windows should be aligned with the UV light source/emitter 712 and UV detector/receiver 714 to ensure that the UV light passes through the window on one side and is detected by the UV detector/receiver 714 on the other side.

It is important to note that each of the above described systems can be implemented as a stand-alone system or on-board system. For example, the systems that isolate the fluid (e.g., those shown in FIGS. 1A-1C, 2A-2D, 3, 8A-8C, and 9A-9C) and the in-line systems (e.g., those shown in FIGS. 11-13) may be stand-alone systems (e.g., they may be separate from the blood processing system) or they may be on-board systems that are integrated with the blood processing system. Similarly, the UV system (e.g., shown in FIG. 14) can be a stand-alone system or integrated with the blood processing system.

Although aspects of embodiments are described above as utilizing microcontrollers to determine the type of fluid, other embodiments may be implemented as computer program instructions (such as software), hardware (such as combinatorial logic, Application Specific Integrated Circuits (ASICs), Field-Programmable Gate Arrays (FPGAs) or other hardware), firmware or combinations thereof. Embodiments may be implemented by a processor executing, or controlled by, instructions stored in a memory. The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-writable storage media (e.g., read-only memory devices within a computer, such as ROM, or devices readable by a computer I/O attachment, such as CD-ROM or DVD disks), information alterably stored on tangible writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A disposable set for a blood processing system comprising:
a first section of tubing configured to fluidly connect a fluid source and a blood processing system;
a first connector configured to connect to the fluid source;
a second connector configured to connect with the blood processing system, wherein fluid can pass from a fluid source through the first connector, the first section of tubing, and finally through the second connector to the blood processing system;
an electrode unit having a housing and a first and second electrode within the housing, the first and second electrode configured to contact fluid passing through the disposable set; and
a second section of tubing, having a first end and a second end, the first end being connected to the first section of tubing at a point between the first connector and the second connector, the second section of tubing branching off; and
a ventilation plug located at the second end of the second section of tubing and configured to allow air to exit the second section of tubing,
wherein the electrode unit is located on the second section of tubing, between the first end and the second end.

2. A disposable set for a blood processing system comprising:
a first section of tubing configured to fluidly connect a fluid source and a blood processing system;
a first connector configured to connect to the fluid source;
a second connector configured to connect with the blood processing system;
an electrode unit having a housing and a first and second electrode within the housing, the first and second electrode configured to contact fluid passing through the disposable set;
a second section of tubing extending from the first section of tubing, the electrode unit located on the second section of tubing; and
a valve located on the second section of tubing and upstream of the electrode unit, the valve configured to prevent fluid in contact with the first and second electrode from re-entering the first section of tubing when closed.

3. A disposable set according to claim 1, further comprising a first collection bag for collecting a first blood component.

4. A disposable set according to claim 1, wherein the second connector is configured to connect to a port on a blood component separation device.

5. A disposable set according to claim 1 further comprising a valve located on the first section of tubing and configured, when closed, to prevent flow of fluid through the disposable set if the first connector is connected to an incorrect fluid source.

6. A disposable set according to claim 1, wherein the electrode unit is configured to interact with a system for detecting a type of fluid, the system configured to determine a type of fluid passing through the disposable set.

7. A disposable set according to claim 6, further comprising a valve located on the first section of tubing and configured to selectively allow and prevent flow of fluid through the disposable set.

8. A disposable set according to claim 7, wherein the operation of the valve is controlled by the system based upon the type of fluid detected.

9. A disposable set according to claim 2, further comprising a ventilation plug located at an end of the second section of tubing and configured to allow air to exit the second section of tubing.

10. A disposable set according to claim 2, further comprising a first collection bag for collecting a first blood component.

11. A disposable set according to claim 2, wherein the second connector is configured to connect to a port on a blood component separation device.

12. A disposable set according to claim 2, further comprising a valve located on the first section of tubing and configured, when closed, to prevent flow of fluid through the disposable set if the first connector is connected to an incorrect fluid source.

13. A disposable set according to claim 2, wherein the electrode unit is configured to interact with a system for detecting a type of fluid, the system configured to determine a type of fluid passing through the disposable set.

14. A disposable set according to claim 13, further comprising a valve located on the first section of tubing and configured to selectively allow and prevent flow of fluid through the disposable set.

15. A disposable set according to claim 14, wherein the operation of the valve is controlled by the system based upon the type of fluid detected.

\* \* \* \* \*